US010723786B2

(12) United States Patent
Beaumont et al.

(10) Patent No.: US 10,723,786 B2
(45) Date of Patent: *Jul. 28, 2020

(54) RSV-SPECIFIC BINDING MOLECULE

(71) Applicant: MedImmune Limited, Cambridge (GB)

(72) Inventors: Tim Beaumont, Ouderkerk aan de Amstel (NL); Adrianus Q. Bakker, Hoorn (NL); Etsuko Yasuda, Amsterdam (NL)

(73) Assignee: MedImmune, Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/047,524

(22) Filed: Jul. 27, 2018

(65) Prior Publication Data

US 2019/0040120 A1 Feb. 7, 2019

Related U.S. Application Data

(63) Continuation of application No. 15/042,656, filed on Feb. 12, 2016, now Pat. No. 10,035,843, which is a continuation of application No. 14/039,148, filed on Sep. 27, 2013, now Pat. No. 9,283,274, which is a continuation of application No. 12/898,325, filed on Oct. 5, 2010, now Pat. No. 8,568,726.

(60) Provisional application No. 61/278,358, filed on Oct. 6, 2009.

(51) Int. Cl.
*C07K 16/10* (2006.01)
*A61K 39/42* (2006.01)
*A61K 31/7088* (2006.01)
*A61K 39/00* (2006.01)

(52) U.S. Cl.
CPC ...... *C07K 16/1027* (2013.01); *A61K 31/7088* (2013.01); *A61K 39/42* (2013.01); *A61K 2039/505* (2013.01); *A61K 2039/507* (2013.01); *C07K 2317/51* (2013.01); *C07K 2317/515* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,517,304 | A | 5/1985 | Stott et al. |
|---|---|---|---|
| 4,526,938 | A | 7/1985 | Churchill et al. |
| 4,659,563 | A | 4/1987 | Dobkin |
| 4,717,766 | A | 1/1988 | Dobkin |
| 4,760,026 | A | 7/1988 | Lennox et al. |
| 4,800,078 | A | 1/1989 | Prince et al. |
| 4,853,326 | A | 8/1989 | Quash et al. |
| 4,917,893 | A | 4/1990 | Okada et al. |
| 5,071,758 | A | 12/1991 | Stott et al. |
| 5,128,326 | A | 7/1992 | Balazs et al. |
| 5,137,804 | A | 8/1992 | Greene et al. |
| 5,149,650 | A | 9/1992 | Wertz et al. |
| 5,183,657 | A | 2/1993 | Buurman |
| 5,194,595 | A | 3/1993 | Wathen |
| 5,219,996 | A | 6/1993 | Bodmer et al. |
| 5,223,254 | A | 6/1993 | Paradiso et al. |
| 5,223,409 | A | 6/1993 | Ladner et al. |
| 5,240,694 | A | 8/1993 | Gwaltney, Jr. |
| 5,271,927 | A | 12/1993 | Parker et al. |
| 5,279,935 | A | 1/1994 | Nycz |
| 5,288,630 | A | 2/1994 | Wathen |
| 5,290,540 | A | 3/1994 | Prince et al. |
| 5,332,567 | A | 7/1994 | Goldenberg |
| 5,332,805 | A | 7/1994 | Carey et al. |
| 5,340,926 | A | 8/1994 | Lowe et al. |
| 5,354,554 | A | 10/1994 | Rhind |
| 5,391,478 | A | 2/1995 | Greene et al. |
| 5,403,484 | A | 4/1995 | Ladner et al. |
| 5,411,749 | A | 5/1995 | Mayo et al. |
| 5,412,077 | A | 5/1995 | Siber et al. |
| 5,418,136 | A | 5/1995 | Miller et al. |
| 5,422,097 | A | 6/1995 | Gwaltney, Jr. |
| 5,424,189 | A | 6/1995 | Oberst et al. |
| 5,468,606 | A | 11/1995 | Bogart et al. |
| 5,470,736 | A | 11/1995 | Verma et al. |
| 5,476,997 | A | 12/1995 | Kaneshima et al. |
| 5,484,893 | A | 1/1996 | Parker et al. |
| 5,496,703 | A | 3/1996 | Babish et al. |

(Continued)

FOREIGN PATENT DOCUMENTS

| AU | 713113 | 11/1999 |
|---|---|---|
| AU | 2002219944 | 2/2008 |

(Continued)

OTHER PUBLICATIONS

Chen et al., "Generation and Analysis of Random Point Mutations in an Antibody CDR2 Sequence: Many Mutated Antibodies Lose Their Ability to Bind Antigen," *J. Exp. Med.*, Sep. 1992; 176:855-866.
U.S. Appl. No. 09/724,396, filed Nov. 28, 2000, Young et al.
U.S. Appl. No. 13/413,609, filed Mar. 6, 2012, Young et al.
Abbas et al., 1991. *Cellular and Molecular Immunology* Chapter 3: "Antibodies and Antigens," p. 4547. WB Saunders Company.
Abman et al., 1988. "Role of Respiratory Syncytial Virus in Early Hospitalizations for Respiratory Distress of Young Infants With Cystic Fibrosis." *J Pediatr.* 113(5):826-30.

(Continued)

*Primary Examiner* — Stacy B Chen
(74) *Attorney, Agent, or Firm* — Mueting, Raasch & Gebhardt, P.A.

(57) ABSTRACT

The invention provides antibodies and functional equivalents thereof which are capable of specifically binding RSV. Nucleic acid sequences encoding said antibody, as well as antibody producing cells and methods for producing said antibody are also provided.

19 Claims, 9 Drawing Sheets

Specification includes a Sequence Listing.

(56) References Cited

U.S. PATENT DOCUMENTS

| | | |
|---|---|---|
| 5,506,209 A | 4/1996 | Mukerji et al. |
| 5,518,725 A | 5/1996 | Daynes et al. |
| 5,530,102 A | 6/1996 | Gristina et al. |
| 5,534,411 A | 7/1996 | Weltzin |
| 5,538,733 A | 7/1996 | Emery et al. |
| 5,538,952 A | 7/1996 | Mukerji et al. |
| 5,571,698 A | 11/1996 | Ladner et al. |
| 5,585,089 A | 12/1996 | Queen et al. |
| 5,624,821 A | 4/1997 | Winter |
| 5,648,260 A | 7/1997 | Winter |
| 5,667,988 A | 9/1997 | Barbas et al. |
| 5,679,377 A | 10/1997 | Bernstein et al. |
| 5,693,762 A | 12/1997 | Queen et al. |
| 5,762,905 A | 6/1998 | Burton et al. |
| 5,811,524 A | 9/1998 | Brams et al. |
| 5,824,307 A | 10/1998 | Johnson |
| 5,840,298 A | 11/1998 | Brams et al. |
| 5,855,913 A | 1/1999 | Hanes et al. |
| 5,866,125 A | 2/1999 | Brams et al. |
| 5,874,064 A | 2/1999 | Edwards et al. |
| 5,912,015 A | 6/1999 | Bernstein et al. |
| 5,916,597 A | 6/1999 | Lee et al. |
| 5,929,212 A | 7/1999 | Joliffe et al. |
| 5,934,272 A | 8/1999 | Lloyd et al. |
| 5,939,068 A | 8/1999 | Brams et al. |
| 5,955,364 A | 9/1999 | Brams et al. |
| 5,958,765 A | 9/1999 | Brams et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,096,551 A | 8/2000 | Barbas et al. |
| 6,117,980 A | 9/2000 | Gonzalez et al. |
| 6,121,022 A | 9/2000 | Presta |
| 6,194,551 B1 | 2/2001 | Idusogie |
| 6,277,375 B1 | 8/2001 | Ward |
| 6,413,771 B1 | 7/2002 | Brams et al. |
| 6,519,948 B2 | 2/2003 | Zorn |
| 6,528,624 B1 | 3/2003 | Idusogie |
| 6,537,809 B2 | 3/2003 | Brams et al. |
| 6,538,124 B1 | 3/2003 | Idusogie |
| 6,565,849 B2 | 5/2003 | Koenig et al. |
| 6,565,888 B1 | 5/2003 | Tracy et al. |
| 6,572,856 B1 | 6/2003 | Taylor et al. |
| 6,656,467 B2 | 12/2003 | Young et al. |
| 6,685,942 B1 | 2/2004 | Burton et al. |
| 6,737,056 B1 | 5/2004 | Presta |
| 6,818,216 B2 | 11/2004 | Young et al. |
| 6,855,493 B2 | 2/2005 | Young et al. |
| 7,083,784 B2 | 8/2006 | Dall'Acqua |
| 7,132,100 B2 | 11/2006 | Oliver et al. |
| 7,179,900 B2 | 2/2007 | Young et al. |
| 7,208,162 B2 | 4/2007 | Prince et al. |
| 7,229,619 B1 | 6/2007 | Young et al. |
| 7,294,336 B2 | 11/2007 | Oliver et al. |
| 7,323,172 B2 | 1/2008 | Young et al. |
| 7,416,726 B2 | 8/2008 | Ravetch |
| 7,425,618 B2 | 9/2008 | Oliver et al. |
| 7,488,477 B2 | 2/2009 | Pilkington et al. |
| 7,553,489 B2 | 6/2009 | Young et al. |
| 7,635,568 B2 | 12/2009 | Young et al. |
| 7,658,921 B2 | 2/2010 | Dall'Acqua et al. |
| 7,670,600 B2 | 3/2010 | Dall'Acqua et al. |
| 7,700,720 B2 | 4/2010 | Tous et al. |
| 7,700,735 B2 | 4/2010 | Young et al. |
| 7,704,497 B2 | 4/2010 | Dall'Acqua et al. |
| 7,740,851 B2 | 6/2010 | Young et al. |
| 7,785,592 B2 | 8/2010 | Oliver et al. |
| 7,847,082 B2 | 12/2010 | Young et al. |
| 8,007,793 B2 | 8/2011 | Oliver et al. |
| 8,012,476 B2 | 9/2011 | Dall'Acqua et al. |
| 8,153,133 B2 | 4/2012 | Young et al. |
| 8,206,951 B2 | 6/2012 | Oliver et al. |
| 8,568,726 B2 | 10/2013 | Beaumont et al. |
| 9,283,274 B2 | 3/2016 | Beaumont et al. |
| 10,035,843 B2 * | 7/2018 | Beaumont .......... C07K 16/1027 |
| 2001/0034062 A1 | 10/2001 | Koenig et al. |
| 2002/0004046 A1 | 1/2002 | Johnson et al. |
| 2002/0018780 A1 | 2/2002 | Koenig et al. |
| 2002/0102257 A1 | 8/2002 | Johnson et al. |
| 2003/0194404 A1 | 10/2003 | Greenfeder et al. |
| 2004/0002587 A1 | 1/2004 | Watkins |
| 2004/0005323 A1 | 1/2004 | Brams et al. |
| 2004/0038878 A1 | 2/2004 | Tanikawa et al. |
| 2004/0076631 A1 | 4/2004 | Brams et al. |
| 2004/0105862 A1 | 6/2004 | Pan et al. |
| 2006/0115485 A1 | 6/2006 | Losonsky et al. |
| 2009/0175883 A1 | 7/2009 | Oliver et al. |
| 2010/0098708 A1 | 4/2010 | Losonsky et al. |
| 2010/0239593 A1 | 9/2010 | Spits et al. |
| 2010/0266614 A1 | 10/2010 | Young et al. |
| 2011/0158985 A1 | 6/2011 | Losonsky et al. |
| 2011/0311454 A1 | 12/2011 | Dall'Acqua et al. |
| 2012/0045456 A1 | 2/2012 | Oliver et al. |
| 2012/0070447 A1 | 3/2012 | Young et al. |
| 2012/0135006 A1 | 5/2012 | Young et al. |
| 2014/0093500 A1 | 4/2014 | Beaumont et al. |
| 2016/0251412 A1 | 9/2016 | Beaumont et al. |

FOREIGN PATENT DOCUMENTS

| | | |
|---|---|---|
| CA | 2197684 | 2/1996 |
| EA | 011669 | 4/2009 |
| EP | 0327378 | 8/1989 |
| EP | 0368684 | 5/1990 |
| EP | 0413622 | 2/1991 |
| EP | 0671927 | 9/1995 |
| EP | 0682040 | 11/1995 |
| EP | 0451216 | 1/1996 |
| EP | 0699756 | 3/1996 |
| EP | 1259547 | 9/2001 |
| EP | 1265928 | 12/2002 |
| EP | 1336410 | 8/2003 |
| EP | 1659133 | 5/2006 |
| EP | 1997830 | 12/2008 |
| EP | 2095827 | 9/2009 |
| FR | 2758331 | 7/1998 |
| JP | 1268646 | 10/1989 |
| RU | 2268266 | 1/2006 |
| RU | 2540020 C2 | 1/2015 |
| WO | WO 90/07861 | 7/1990 |
| WO | WO 91/05548 | 5/1991 |
| WO | WO 92/05274 | 4/1992 |
| WO | WO 92/19244 | 11/1992 |
| WO | WO 93/05796 | 4/1993 |
| WO | WO 93/15199 | 8/1993 |
| WO | WO 93/15200 | 8/1993 |
| WO | WO 93/19197 | 9/1993 |
| WO | WO 93/20210 | 10/1993 |
| WO | WO 94/06448 | 3/1994 |
| WO | WO 94/29351 | 12/1994 |
| WO | WO 95/04081 | 2/1995 |
| WO | WO 96/05229 | 2/1996 |
| WO | WO 96/20698 | 7/1996 |
| WO | WO 96/40252 | 12/1996 |
| WO | WO 97/32572 | 9/1997 |
| WO | WO 97/34631 | 9/1997 |
| WO | WO 97/44013 | 11/1997 |
| WO | WO 98/23289 | 6/1998 |
| WO | WO 98/31346 | 7/1998 |
| WO | WO 98/31807 | 7/1998 |
| WO | WO 98/33919 | 8/1998 |
| WO | WO 98/34594 | 8/1998 |
| WO | WO 99/15154 | 4/1999 |
| WO | WO 99/20253 | 4/1999 |
| WO | WO 99/28471 | 6/1999 |
| WO | WO 99/51642 | 10/1999 |
| WO | WO 99/66903 | 12/1999 |
| WO | WO 00/29584 | 5/2000 |
| WO | WO 00/42072 | 7/2000 |
| WO | WO 00/56771 | 9/2000 |
| WO | WO 00/69462 | 11/2000 |
| WO | WO 00/73346 | 12/2000 |
| WO | WO 01/55217 | 8/2001 |

(56) References Cited

FOREIGN PATENT DOCUMENTS

| | | |
|---|---|---|
| WO | WO 01/58957 | 8/2001 |
| WO | WO 01/64751 | 9/2001 |
| WO | WO 01/77137 | 10/2001 |
| WO | WO 02/011753 | 2/2002 |
| WO | WO 02/43660 | 6/2002 |
| WO | WO 02/060919 | 8/2002 |
| WO | WO 03/052083 | 6/2003 |
| WO | WO 03/054213 | 7/2003 |
| WO | WO 2003/080672 | 10/2003 |
| WO | WO 2004/010935 | 2/2004 |
| WO | WO 2004/016750 | 2/2004 |
| WO | WO 2004/029207 | 4/2004 |
| WO | WO 2004/035752 | 4/2004 |
| WO | WO 2004/043989 | 5/2004 |
| WO | WO 2004/083373 | 9/2004 |
| WO | WO 2005/030124 | 4/2005 |
| WO | WO 2005/079479 | 9/2005 |
| WO | WO 2006/034292 | 3/2006 |
| WO | WO 2007/002543 | 1/2007 |
| WO | WO 2007/067046 | 6/2007 |
| WO | WO 2008/147196 | 12/2008 |
| WO | WO 2009/003019 | 12/2008 |
| WO | WO 2009/030237 | 3/2009 |
| WO | WO 2009/114815 | 9/2009 |
| WO | WO 2011/043643 | 4/2011 |

OTHER PUBLICATIONS

Adams et al., 1998. "Increased affinity leads to improved selective tumor delivery of single-chain Fv antibodies." *Cancer Res.* 58(3):485-90.
Adams et al., 1998. "Prolonged in vivo tumour retention of a human diabody targeting the extracellular domain of human HER2/neu." *Br J Cancer.* 77(9):140512.
American Academy of Pediatrics Committee on Infectious Diseases, "Use of Ribavirin in the Treatment of Respiratory Syncytial Virus Infection." *Pediatrics,* Sep. 1993;92(3):501-4.
*American Heritage Dictionary of the English Language,* Fourth Edition, Houghton Mifflin Company. 2000; p. 574 ("elderly"), p. 12234 ("old").
Ames et al., 1995. "Conversion of murine Fabs isolated from combinatorial phage display library to full length immunoglobulins." *J Immunol Methods.*184(2):177-86.
Anderson et al., 1985. "Microneutralization test tor respiratory syncytial virus based on an enzyme immunoassay." *J Clin Microbiol.* 22:1050-1052.
Arbiza et al., 1992. "Characterization of two antigenic sites recognized by neutralizing monoclonal antibodies directed against the fusion glycoprotein of human respiratory syncytial virus." *J Gen Virol.* 73: 2225-2234.
Balint and Larrick, 1993. "Antibody engineerine by parsimonious mutagenesis." *Gene.* 137(1):109-118.
Barbas et al., 1992 "Human monoclonal Fab fragments derived from a combinatorial library bind to respiratory svncytial virus F glycoprotein and neutralize infectivity," *Proc Natl Acad Sci USA.* 89(21):10164-8.
Barbas et al., 1996. "Selection and evolution of high-affinity human antiviral antibodies." *Trends Biotech.* 14(7):230234.
Bebbington et al., 1992, "High-level expression of a recombinant antibody from myeloma cells using a glutamine synthetase gene as an amplifiable selectable marker", *Biotechnology* (N Y). 10(2):169-75.
Beeler et al., 1989. "Neutralization Epitopes of the F Glycoprotein of Respiratory Syncytial Virus: Effect of Mutation Upon Fusion Function." *J Virol.* 63(7):2941-50.
Bennett et al., 2007. "Immunopathogenesis of Respiratory Syncytial Virus Bronchiolitis." *J Infect Dis.* 195(10):1532-1540.
Bentley and Rabbitts, 1980. "Human immunoglobulin variable region genesDNA Sequences of Two V Kappa Genes and a Psoudogene." *Nature* 288: 730-733.

Berzofsky and Berkower, 1993. in Paul, W.E., *Fundamental Immunology* (Raven Press), Chapter 8: "Immunogenicity and antigen structure," p. 242.
Berzoesky and Berkower, 1993. in Paul, W.E., *Fundamental Immunology* (Raven Press), Chapter 9: "Structure and Function of Immunoglobulins," p. 292295.
Better et al., 1988. "*Escherichia coli* secretion of an active chimeric antibody fragment." *Science.* 240(4855):1041-3.
Blake et al., 1999. "Automated Kinetic Exclusion Assays to Quantify Protein Binding Interactions in Homogeneous Solution." *Analytical Biochemistry* 272: 1231-34.
Boder et al., 2000. "Directed evolution of antibody fragments with monovalent femtomolar antigen-binding affinity." *Proc Natl Acad Sci USA.* 97(20):10701-5.
Boeckh et al., 2001. "Phase 1 Evaluation of the Respiratory Syncytial Virus-Specific Monoclonal Antibody Palivizumab in Recipients of Hematopoietic Stem Cell Transplants." *J of Infect Dis.* 184: 350-354.
Boulianne et al., 1984. "Production of functional chimaeric mouse/human antibody." *Nature* 312(5995):643-646.
Bourgeois et al., "New peptides recognizing viral epitopic with tropism to mucosa-useful for, e.g. diagnosing, preventing and treating viral infection(s)." GENESEQ database entry for Accession No. AAW70933; Oct. 14, 1998 and alignment with Seq ID No. 12 of U.S. Appl. No. 09/771,415.
Brinkmann et al., 1995. "Phage display of disulfide-stabilized Fv fragments." *J Immunol Methods.* 182(1):41-50.
Burton and Barbas, 1994. "Human antibodies from combinatorial libraries." *Adv. Immunol.* 57:1912-80.
Cao et al., 2003. "Bispecific antibody conjugates in therapeutics." *Adv Drug Deliv Rev.* 55(2): 17197.
Carlsson et al., 1992, "Human peripheral blood lymphocytes transplanted into SCID mice constitute an in vivo culture system exhibiting several parameters found in a normal humoral immune response and are a source of immunocytes for the production of human monoclonal antibodies." *J Immunol.* 148(4): 1065-71.
Carson and Freimark, 1986, "Human lymphocyte hybridomas and monoclonal antibodies," *Adv Immunol.* 38:275-311.
Casset et al., 2003. A peptide mimetic of an antiCD4 monoclonal antibody by rational design. *Biochem Biophys Res Commun.* 307(1): 198-205.
Chamat et al., 1999. "Human monoclonal antibodies isolated from spontaneous Epstein-Barr Virus-transformed tumors of HuSPL-SCID mice and specific for fusion protein display broad neutralizing activity toward respiratory syncytial virus." *J Infect Dis.* 180:268-277.
Chanock et al., 1989. "Respiratory syncytial virus. Viral Infections of Humans, Epidemiology and Control," 3rd Evans, ed., A.S. Chapter 20:525-544.
Chmura et al., 2001. "Antibodies with infinite affinity." *Proc Nat Acad Sci.* 98(15):8480-8484.
Chothia et al., 1998. "Structural determinants in the sequences of immunoglobulin variable domain." *J Mol Biol.* 278(2):457-79.
Chowdhury et al., 2005. "Tailor-made antibody therapeutics." *Methods.* 36:11-24.
Cleek et al., 1997. "Biodegradable Polymeric Carriers for a bFGF Antibody for Cardiovascular Application." *Pro Int'l Symp Control Rel Bioact Mater.* 24:853-854.
Colman, 1994. "Effects of amino acid sequence changes on antibodyantigen interactions." *Res Immunol.* 145(1):33-6.
Connors, 1990. *Chemical Kinetics: The Study of Reaction Rates in Solution.* p. 152.
Conrad et al., 1987. "Aerosolized ribavirin treatment of respiratory syncytial virus infection in infants hospitalized during an epidemic." *Pediatr Infect Dis J.* 6(2):1521-58.
Crowe et al., 1094. "Recombinant human respiratory syncytial virus (RSV) monoclonal antibody Fab is effective therapeutically when introduced directly into the lungs of RSV-infected mice." *Proc Natl Acad Sci USA.* 91:1386-1390.
Crowe et al., 1998. Monoclonal antibody-resistant mutants selected with a respiratory syncytial virus-neutralizing human antibody fab fragment (Fab 19) define a unique epitope on the fusion (F) glycoprotein. *Virology.* 252(2):373-5.

(56) References Cited

OTHER PUBLICATIONS

Cruse and Lewis, 1995. *Illustrated Dictionary of Immunology*. Boca Raton: CRC Press. pp. 18-19.
Dall'Acqua, 2002. "Increasing the Affinity of a Human IgG1 for the Neonatal Fc Receptor: Biological Consequences." *J of Immunol.* 169: 5171-5180.
De Vincenzo et al., 2005. "Factors Predicting Childhood Respiratory Syncytial Virus Severity—What They Indicate About Pathogenesis." *Ped Inf Dis J*.24:S177-S183.
Delagrave et al., 1999. "Effects of humanization by variable domain resurfacing on the antiviral activity of a single-chain antibody against respiratory syncytial virus." *Protein Eng.* 12(4):357-62.
DGene Database Accession No. AWJ00720, "Human anti-RSV antibody light chain (VL) protein clone 744 SEQ ID:91", dated May 14, 2009.
*Dorland's Illustrated Medical Dictionary*, 1994, 28th ed., Philadelphia: WB Saunders p. 874.
Downham et al., 1976. "Breastfeeding protects against respiratory syncytial virus infections." *Br Med J.* 2(6030):274-6.
Duenas et al., 1996. "In vitro immunization of naive human B cells yields high affinity immunoglobulin G antibodies as illustrated by phage display." *Immunology.* 89(1):1-7.
Duenas et al., 1996. "Selection of phage displayed antibodies based on kinetic constants." *Mol Immunol.* 33(3):279-85.
Edelman et al., 1969. "The Covalent Structure of an Entire gammaG Immunoglobulin Molecule." *PNAS* 63:78-85.
Egan et al., 1999, "Effect of Sch 55700, a humanized monoclonal antibody to human interleukin5, on eosinophilic responses and bronchial hyperreactivity." *Arzneimittelforschung.* 49(9):779-790.
"Elderly", Wikipedia, the free encyclopedia, [retrieved on Jul. 27, 2017]. Retrieved from the Internet: <https://en.wikipedia.org/wiki/elderly>; 2 pages.
Ettinger el al., 2005 "IL21 induces differentiation of human naive and memory B cells into antibody-secreting plasma cells," *J Immunol.* 175(12):78677-9.
Evans, 1989. "Viral Infections of Humans," *Epidemiology and Control.* 3rd ed., 52544.
Everitt et al., 1996. "The pharmacokinetics, antigenicity, and fusion-inhibition activity of RSHZ19, a humanized monoclonal antibody to respiratory syncytial virus, in healthy volunteers." *J Infect Dis.* 174:463-469.
Fahy and O'Byrne, 2001. "Reactive Airways Disease." *Am J Respir Crit Care Med.* 163(4):822-3.
Falsey. 1991. "Noninfluenza Respiratory Virus Infection in Long-Term Care Facilities." *Infect Control Hosp Epidemiol.* 12(10):602-608.
Feigen et al., 1987. In: *Textbook of Pediatric Infectious Diseases*, WB Saunders, Philadelphia, at pp. 1653-1675; "New Vaccine Development, Establishing Priorities," vol. 1, 1985, National Academy Press, Washington D.C. at pp. 397-409.
Fields et al., 1990. *Fields Virology*, 2nd Ed., vol. 1, Raven Press, NY p. 1045-1072.
Fields et al., 1996. "Crystal Structure of the V-alpha domain of a T cell antigen receptor." *Immunotechnology* 2(4):270.
Fisher et al., 1999, "Passive IgA monoclonal antibody is no more effective than IgG at protecting mice from mucosal challenge with respiratory syncytial virus," *J. Infect Dis.*, 180(4): 1324-7.
Foecking and Hoestetter, 1986. "Powerful and versatile enhancer-promoter unit for mammalian expression vectors." *Gene.* 45:101-105.
Foote et al., 1991. "Kinetic maturation of an immune response." *Nature* 352:530-532.
Foote et al., 1995. "Kinetic and affinity limits on antibodies produced during immune response." *Proc Nat'l Acad Science USA.* 92:1254-1256.
Garcia-Barreno et al., 1989. "Marked Differences in the Antigenic Structure of Human Respiratory Syncytial Virus F and G Glycoproteins." *J Vivol.* 63(2):925-32.
Garvie and Gray, 1980. "Outbreak of Respiratory Syncytial Virus Infection in the Elderly." *Br Med J.* 281(6250): 12534.
Gilchrist, et al. 1994. "National surveillance for respiratory syncytial virus, United States, 1985-1990." *J Infect Dis.* 170:986-990.
Gillies et al., 1989. "High-level expression of chimeric antibodies using adapted cDNA variable region cassettes." *J Immunol Methods.* 125:191-202.
Glaser et al., 1992. "Antibody engineering by codon-based mutagenesis in a filamentous phage vector system." *J Immunol.* 149: 3903-3913.
Glezen et al., 1981. "Risk of Respiratory Syncytial Virus Infection for Infants From Low-Income Families in Relationship to Age, Sex, Ethnic Group, and Maternal Antibody Level." *J Pediatr.* 98(5):708-15.
Greenspan et al., 1999. "Defining epitopes: It's not as easy as it seems." *Nature Biotechnology.* 17:936-937.
Groothuis et al., 1988. "Respiratory Syncytial Virus Infection in Children with Broncho-pulmonary Dysplasia."*Pediatrics*. 82(2):199-203.
Groothuis et al., 1993. "Prophylactic Administration of Respiratory Syncytial Virus Immune Globulin to High-risk Infants and Young Children." The Respiratory Syncytial Virus Immune Globulin Study Group. *N Engl J Med.* 329(21):1524-1530.
Groves et al., 1987. "Production of an ovine monoclonal antibody to testosterone by an inter-species fusion." *Hybridoma* 6(1):71-76.
Hacking and Hull, 2002. "Respiratory syncytial virus-viral biology and the host response." *J Infect.* 45(1):18-24.
Hall et al., 1975. "Nosocomial respiratory syncytial virus infections." *N. Engl. J. Med.* 293(26): 1343-1346.
Hall et al., 1979. "Neonatal Respiratory Syncytial Virus Infection." *N. Engl. J. Med.* 300(8):393-6.
Hall et al., 1983. Aerosolized ribavirin treatment of infants with respiratory syncytial viral infection. A randomized double-blind study. *N Engl J Med.* 308(24):1443-1447.
Hall et al., 1985. "Ribavirin treatment respiratory syncytial viral infection in infants with underlying cardiopulmonary disease." *JAMA* 254(21):3047-3051.
Hall et al., eds., 1995. "Principles and Practice of Infectious Diseases." 4th ed., Churchill Livingstone, New York, pp. 1501-1519.
Hall, 1987. "Respiratory syncytial virus." *Textbook of Pediatric Infectious Diseases*, Feigin and Cherry, eds., WB Saunders, Philadelphia, 1653-1676.
Hall, C.B., 1993. "Respiratory Syncytial Virus: What We Know Now." *Contemp Pediatrics.* 10:92110.
Hammerling et al., 1981. "Production of Antibody-Producing Hybridomas in the Rodent Systems," in *Monoclonal Antibodies and T-Cell Hybridomas*, Elsevier, NY. p. 563-587.
Haynes et al., 2002. "Neutralizing anti-F glycoprotein and anti-substance P antibody treatment effectively reduces infection and inflammation associated with respiratory syncytial virus infection." *J Virol.* 76(14):6873-6881.
Heard et al., 1999. "Two Neutralizing Human Anti RSV Antibodies: Cloning, Expression and Characterization." *Molec. Med.* 5:35-45.
Hefta et al, 1998. "Kinetic and affinity constants of epitope specific anti-carcinembryonic antigen (CEA) monoclonal antibodies for CEA and engineered CEA domain constructs." *Immunotechnology* 4:49-57.
Hellstrom et al., 1987. "Antibodies for drug delivery." *Controlled Drug Delivery, Fundamentals and Applications* 2nd edition. Chapter 15: p. 623-653.
Hemming et al., 1985. "Studies of Passive Immunotherapy for Infections of Respiratory Syncynal Virus in the Respiratory Tract of a Primate Model," *J Infect Dis.* 152(5):10837.
Hemming et al., 1986. "Immunoglobulins in respiratory syncytial virus infections." *Clinical Use of Intravenous Immunoglobulins*, Morell and Nydegger., eds., Academic Press, London, pp. 285-294.
Hemming et al., 1988. "Topically Administered Immunoglobulin Reduces Pulmonary-Respiratory Syncytial Virus Shedding in Owl Monkeys." *Antimicrob Agents Chemother.* 32(8): 1269-1270.
Henderson et al., 1979. "Respiratory-Syncytial-Virus Infections, Reinfections and Immunity. A Prospective, Longitudinal Study in Young Children." *N Engl J Med.* 300(10):530-4.

(56) References Cited

OTHER PUBLICATIONS

Hertz et al., 1989. "Respiratory Syncytial Virus-Induced Acute Lung Injury in Adult Patients With Bone Marrow Transplants: a Clinical Approach and Review of the Literature." *Medicine* (Baltimore). 68(5):2698.
Howard et al., 1989."Intracerebral Drug Delivery in Rats with Lesion-Induced Memory Deficits." *J Neurosurg*. 71(1):105-12.
Hudson and Souriau, 2003. "Engineered Antibodies." *Nature Medicine* 9(1): 129-34.
Ichiyoshi et al., 1995. "A human anti-insulin IgG autoantibody apparently arises through clonal selection from an insulin-specific "germline" natural antibody template. Analysis by V gene segment reassortment and site-directed mutagenesis." *J Immunol*. 154(1):22638.
Ifverson and Borrebaeck, 1996. "SCIDhuPBL: a model for making human antibodies?" *Semin Immunol*. 8(4):2438.
Jackson et al., 1998. "Antigen specificity and tumour targeting efficiency of a human carcinoembryonic antigen-specific scFv and affinity-matured derivatives." *Br. J. Cancer*. 78(2): 181-8.
Johnson et al., 1987. "The G Glycoprotein of Human Respiratory Syncytial Viruses of Subgroups A and B: Extensive Sequence Divergence Between Antigenically Related Proteins." *Proc Natl Acad Sci USA*. 84(16):56259.
Johnson et al., 1991. "Development of humanized monoclonal antibodies which neutralize respiratory syncytial virus." *J Cellular Biochem* Suppl. 15E. p. 120, Abstract No. 108.
Johnson et al., 1997 "Development of a Humanized Monoclonal Antibody (MEDI493) With Potent In Vitro and In Vivo Activity Against Respiratory Syncytial Virus," *J Infect Dis*. 176(5):1215-24.
Johnson et al., 1999. "A direct comparison of the activities of two humanized respiratory syncytial virus monoclonal antibodies: MEDI493 and RSH719." *J. Infect. Dis*. 180(1):3540.
Johnson et al, 2000, "Kabat database and its applications: 30 years after the variability plot." *Nucleic Acids Res*. 28(1):2148.
Kabat et al. 1991, *Sequences of Proteins of Immunological Interest*, Fifth Edition, NIH Publication No. 913242, pp. 679-687.
Kapikian et al., 1969. "An Epidemiologic Study of Altered Clinical Reactivity to Respiratory Syncytial (RS) Virus Infection in Children Previously Vaccinated With an Inactivated RS Virus Vaccine." *Am J Epidemiol*. 89(4):405-21.
Karlsson et al., 1997. "Experimental design for kinetic analysis of protein-protein interactions with surface plasmon resonance biosensors." *J Immunol Meth*. 200:121-133.
Kettleborough et al., 1994. "Isolation of tumor cell-specific single-chain Fv from immunized mice using phage-antibody libraries and the reconstruction of whole antibodies from these antibody fragments." *Eur J Immunol*. 24(4):952-8.
Kim et al., 1969. "Respiratory Syncytial Virus Disease in Infants Despite Prior Administration of Antigenic Inactivated Vaccine." *Am J Epidemiol*. 89(4):422-34.
Kingston, 2003, "Chapter 9: Introduction of DNA into Mammalian Cells", in *Current Protocols in Molecular Biology*, John Wiley & Sons, pp. 9.0.1-9.0.5.
Kipriyanov and Little, 1999, "Generation of Recombinant Antibodies", *Mol Biotechnol*., 12(2):173-201.
Knappik et al., 2000. "Fully synthetic human combinatorial antibody lihraries (HuCAL) based on modular consensus frameworks and CDRs randomized with trinucleotides." *J Mol Biol*. 296(1):5786.
Krishnan et al., 2008. "Therapeutic addition of motavizumab, a monoclonal antibody against respiratory syncytial virus (RSV), modulates epithelial cell responses to RSV infection." *Annual Interscience Conf Antimicrobial Agents Chemotherapy/Annual Meeting Infect Dis Soc Am*. 48/46 Oct. 28 Abstract V4147.
Kudo et al., 1992. "New strategies to establish human monoclonal antibodies." *Tohoku J Exp Med*. 168(2):323-327.
Kudo et al., 1993. "Production of a human monoclonal antibody to a synthetic peptide by active in vivo immunization using a SCID mouse grafted with human lymphocytes." *Tohoku J Exp Med*. 171: 327-338.
Kunkel et al., 1987. "Rapid and efficient site-specific mutagenesis without phenotypic selection." *Methods Enzymol*. 154:367-382.

Lagos et al., 2005. "Administration of the anti-RSV monoclonal antibody (Mab) Numax™, is associated with a reduction in upper airway (UA) RSV load." *World Congress Pediatr Infect Disease*. Sep. 14.
Lam et al., 1997. "Microencapsulation of Recombinant Humanized Monoclonal Antibody for Local Delivery." *Proc Int'l Symp Control Rel Bioact Mater*. 24:759-760.
Lamprecht et al., 1976. "Role of Maternal Antibody in Pneumonia and Bronchiolitis Due to Respiratory Syncytial Virus." *J Infect Dis*. 134(3):211-7.
Landry et al., "Evaluation of reconstituted lyophilized palivizumab given ntravenously at 15 and 30 mg/kg. Pediatric Research," 45 (4 Pt 2: 166A, 969) *Annual Meeting of the American Pediatric Society and the Society for Pediatric Research*, San Francisco, California, USA, May 14, 1999 Poster Session (poster 87).
Langer and Peppas, 1983. Chemical and physical structure of polymers as carriers for controlled release of bioactive agents: a review, *J Macromol Sci.Rev Macromol Chem Phys*.C23(1):611-26.
Langer. 1990. "New methods of drug delivery." *Science*. 249:1527-1533.
Lee et al., 1998. "Demonstration of IgM antibodies or high affinity within the anti-Galα13Gal antibody repertoire." *Transplantation*. 66(8):1117-9.
Levy et al., 1985. "Inhibition Calcification of Bioprosthetic Heart Valves by Local Controlled-release Diphosphonate." *Science*. 228(4696):1902.
Liu et al., 1987."Expression of mouse::human immunoglobulin heavy-chain cDNA in lymphoid cells." *Gene* 54(1):33-40.
Lobuglio et al., 1989. "Mouse/human chimeric monoclonal antibody in man: kinetics and immune response." *Proc Natl Acad Sci USA*. 86(11):4220-4224.
Lonberg and Huszar, 1995. "Human antibodies from transgenic mice." *Int. Rev. Imnnunol*. 13:6593.
Love et al., 1993. "How the anti(metal chelate) antibody CHA255 is specific for the metal ion of its antigen: X-ray structures for two Fab'/hapten complexes with different metals in the chelate." *Biochemistry*. 32(41): 10950-10959.
MacCallum et al., 1996. "Antibody-antigen interactions: contact analysis and binding site topography." *J Mol Biol*. 262(5):732-45.
MacDonald et al., 1982. "Respiratory Syncytial Viral Infection in Infants With Congenital Heart Disease." *N Engl J Med*. 307(7):397-400.
Malley et al., 1998. "Reduction of Respiratory Syncytial Virus (RSV) in Tracheal Aspirates in Intubated Infants by Use of Humanized Monoclonal Antibody to RSV F Protein." *J of Infect Dis*. 178:1555-1561.
Marks et al., 1992. "Bypassing immunization: building high affinity human antibodies by chain shuffling." *Biotechnology* (NY) 10(7):779-83.
Matsuoka et al., 2002, "Characteristics of immunity induced by viral antigen or conferred by antibody via different administration routes," *Clin Exp Immunol*, 130(3):386-92.
Maynard et al., 2002. "Protection against anthrax toxin by recombinant antibody fragments correlates with antigen affinity." *Nat Biotechnol*. 20(6):597-601.
McArthurvaughan et al., 2002. "A *Rhesus* monkey model of respiratory syncytial virus infection." *J. Med. Primatol*. 31(2):61-73.
McCall et al., 1999. "Isolation and characterization of an antiCD16 single-chain Fv fragment and construction of an antiHER2/neu/ antiCD16 bispecific scFv that triggers CD16-dependent tumor cytolysis." *Mol Immunol*. 36(7):433-46.
MedImmune, Inc, 1999 SYNAGIS (registered trademark) package insert, revised Dec. 2, 1999.
MedImmune, Inc. Annual Report (2001).
MedImmune, Inc's (MEDI) phase 1 Numax study shows potential to reduce RSV disease in upper airway of children. (Sep. 1, 2005) BioSpace Beat, Biospace.com (www.biospace.com/news.sub.story.aspx?StoryID=21014020).
MedImmune, Inc's (MEDI) Release: Numax achieves primary endpoint in preliminary analysis of data from comparartive phase 3 trial with Synagis (Nov. 6, 2006) BioSpace Beat, Biospace.com (www.biospace.com/news.sub.story.aspx?StoryID=36114&full=1).

(56) References Cited

OTHER PUBLICATIONS

MedImmune, SYNAGIS (registered trademark) package insert, last revised Oct. 23, 2002.
Meissner et al., 1999. "Safety and pharmacokinetics of an intramuscular monoclonal antibody (SB 209763) against respiratory syncytial virus (RSV) in infants and young children at risk for severe RSV disease." *Antimicrob Agents Chemother*. 43(5):118-38.
Mejias et al., 2005. "Comparative Effects of Two Neutralizing Anti-Respiratory Syncytial Virus (RSV) Monoclonal Antibodies in the RSV Murine Model: Time versus Potency." *Antimicrobial Agents and Chemotherapy*. 49(11): 4700-4707.
Mejias et al., 2005. "Respiratory syncytial virus infections: Old challenges and new opportunities." *Ped. Infect. Dis. J*. 24:S189-S197.
Morell et al., 1986. *Clinical Use of Intravenous Immunuglobulins*. Academic Press, London, pp. 285-294.
Morrison et al., 1984. "Chimeric human antibody molecules: mouse antigen-binding domains with human constant region domains." *Proc. Natl. Acad. Sci. USA* 81(21):6851-6855.
Morrison et al., 1985. "Transfectomas provide novel chimeric antibodies." *Science* 229(4719):1202-1207.
"Motavizumab vs palivizumab for RSV infections in infants," (Nov. 11, 2006) *Inpharna* vol. 1 No. 1563, p. 5.
Mullinax et al., 1992. "Expression of a heterodimeric Fab antibody protein in one cloning step." *Bio Techniques*. 12:864-869.
Murphy et al., 1988. "Passive Transfer of Respiratory Syncytial Virus (RSV) Antiserum Suppresses the Immune Response to the RSV Fusion (F) and Large (G) Glycoproteins Expressed by Recombinant Vaccinia Viruses." *J Virol*. 62(10):3907-10.
Murphy et al., 1991. "Effect of Passive Antibody on the Immune Response of Cotton Rats to Purified F and G HG Glycoproteins of Respiratory Syncytial Virus (RSV)." *Vaccine*. 9(3): 1859.
Murphy et al., 1994. "An Update on Approaches to the Development of Respiratory Syncytial Virus (RSV) and Parainfluenza Virus Type 3 (PIV3) Vaccines." *Virus Res*. 2(1):1336.
Murray et al., 1993. "Biochemistry of the Human" (in the Russian language translation "Biokhimiya Cheloveka"), Moscow: Mir Publ., 1:34.
Myszka et al., 1997. "Kinetic analysis of a protein antigen-antibody interaction limited by mass transport on an optical biosensor." *Biophys Chem*. 64(13):127-37.
Myszka et al., 1999. Survey of the 1998 optical biosensor literature. J. Mol. Recog. 12:390408.
Navas et al., 1992. "Improved Outcome of Respiratory Syncytial Virus Infection in a High-Risk Hospitalized Population of Canadian children. Pediatric Investigators Collaborative Network on Infections in Canada." *J Pediatr*. 121(3):348-54.
Newman et al., 1992. "'Primatization' of recombinant antibodies for immunotherapy of human diseases: A Macaque/Human chimeric antibody against human CD4." *Biotechnol*. 10:1455-1460.
Nguyen et al., 2000. "Efficient generation of respiratory syncytial virus (RSV)neutralizing human MoAbs via human peripheral blood lymphocyte (huPBL) SCID mice and scFv phage display libraries." *Clin. Exp. Immunol*. 122:8593.
Ning et al., 1996. "Intratumoral Radioimmunotherapy of a Human Colon Cancer Xenograft Using a Sustained Release Gel." *Radiotherapy and Oncology* 39: 179-89.
Norderhaug et al., 1997, "Versatile vectors for transient and stable expression of recombinant antibody molecules in mammalian cells", *J. Immunolo. Methods*, 204:77-87.
O'Byrne and Postma, 1999. "The Many Faces of Airway Inflammation." *Am J Respir Crit Care Med*. 159(5 Pt 2):S4163.
Ogra et al., 1988. "Respiratory Syncytial Virus Infection and the Immunocompromised Host." *Pediatr Infect Dis J*. 7(4):2469.
Ohno et al., 1985, "Antigen-binding specificities of antibodies primarily determined by seven residues of VH", *Proc Natl Acad Sci USA*; 82:29452949.
Orkin and Motulsky, 1995 "Report and recommendations of the panel to assess the NIH investment in research on gene therapy," available from http://www.nih.gov/news/panelrep.html.

Ozaki et al., 2004 "Regulation of B cell differentiation and plasma cell generation by IL21, a novel inducer of Blimp1 and Bc16," *J Immunol*. 173(9):536171.
Padlan, 1991. "A possible procedure for reducing immunogenicity of antibody variable domains while preserving their ligand-binding properties." *Mol. Immunol*. 28(4/5):489-498.
Palomo et al., 1990. "Induction of a Neutralizing Immune Response to Human Respiratory Syncytial Virus with Anti-Idiotypic Antibodies." *J. Virology* 64(9): 4199-4206.
Persic et al., 1997. "An integrated vector system for the eukaryotic expression of antibodies or their fragments after selection from phage display libraries." *Gene*. 187(1):918.
*Physician's Desk Reference*, 2001, 55th ed. p. 1863-1864.
Plotnicky-Gilquin et al., 2002 "Passive transfer of serum antibodies induced by BBG2Na, a subunit vaccine, in the elderly protects SCID mouse lungs against respiratory syncytial virus challenge," *Virology*, 10;303(1):130-7.
Pohl et al., 1992. "Respiratory Syncytial Virus Infections in Pediatric Liver Transplant Recipients." *J Infect Dis*. 165(1): 166-9.
Press et al., 1970. "The Amino Acid Sequences of the Fd Fraements of Two Human GammaI Heavy chains." *Biochem J*. 117(4):641-60.
Prince et al., 1983. "Mechanisms of Immunity to Respiratory Syncytial Virus in Cotton Rats." *Infect Immun*. 42(1):81-7.
Prince et al., 1985. "Immunoprophylaxis and Immunotherapy or Respiratory Syncytial Virus Infection in the Cotton rat." *Virus Res*. 3(3):193-206.
Prince et al., 1985. "Quantitative Aspects or Passive Immunity to Respiratory Syncytial Virus Infection in Infant Cotton Rats." *J Virol*. 55(3):517-20.
Prince et al., 1987. "Effectiveness of Topically Administered Neutralizing Antibodies in Experimental Immunotherapy of Respiratory Syncytial Virus Infection in Cotton Rats." *J Virol*. 61(6): 1851-1854.
Prince et al., 1990. Mechanism of Antibody-mediated Viral Clearance in Immunotherapy of Respiratory Syncytial Virus Infection of Cotton Rats. *J Virol*. 64(6):309-12.
Prince et al., 1996. "Treatment of parainfluenza virus type 3 bronchiolitis and pneumonia in a cotton rat model using topical antibody and glucocorticosteroid," *J. Infect. Dis*. 173:598-608.
Prince et al., 2000. "Treatment of Respiratory Syncytial Virus Bronchiolitis and Pneumonia in a Cotton Rat Model with Systematically Administered Monoclonal Antibody (Palivizumab) and Glucocorticosteroid." *J Inf Diseases* 182:1326-1330.
Prince, 1975. "The Pathogenesis of Respiratory Syncytial Virus Infection in Infant Ferrets." Ph.D. Dissertation, University of California Los Angeles.
Prince, 2001. "An update on respiratory syncytial virus antiviral agents." *Expert Opin Investig Drugs*. 10(2):297-308.
Raman et al., 1992. "Diffusion-limited rates for monoclonal antibody binding to cytochrome." *Biochem*. 31:10370-10379.
Reijic et al., 2000 "Suppression of signal transducer and activator of transcription 3dependent B lymphocyte terminal differentiation by BCL6," *J Exp Med*. 192(12):1841-8.
Richter et al., 2008. "Respiratory syncytial virus (RSV) therapy utilizing intranasally delivered motavizumab, a monoclonal antibody against F protein." *Annual Interscience Conf Antimicrobial Agents Chemotherapy/Annual Meet Infect Dis Soc Am*. 48/46 Oct. 28 Abstract V4145.
Riechmann et al., 1988 "Reshaping human antibodies for therapy." *Nature* 32(6162):323-7.
Roguska et al., 1994. "Humanization of murine monoclonal antibodies through variable domain resurfacing." *Proc. Natl. Acad. Sci. U.S.A*. 91(3):969-973.
Roost et al., 1995. "Early high-affinity neutralizing antiviral IgG responses without further overall improvements of affinity." *Proc. Natl. Acad. Sci. USA*. 92:1257-1261.
Roskos et al., 2004, "The clinical pharmacology of therapeutic monoclonal antibodies," *Drug Development Research* 61:108-120.
Rosok et al., 1995. "A combinatorial library strategy for the rapid humanization of anticarcinoma BR 96 Fab." *J. Biol. Chem*. 271(27):22611-22618.
Rudikoff et al., 1982. "Single amino acid substitution altering antigen-binding specificity." *Proc. Natl. Acad. Sci. USA* 79(6):1979-1983.

(56) References Cited

OTHER PUBLICATIONS

Ruther and Muller-Hill, 1983. "Easy identification of cDNA clones." *EMBO J.* 2:1791-1794.
Ruuskanen et al., 1993. "Respiratory syncytial virus." *Curr Probl Pediatr.* 23(2):507-9.
Saez Llorens et al., 1998. "Safety and pharmacokinetics of an intramuscular humanized monoclonal antibody to respiratory syncytial virus in premature infants and infants with bronchopulmonary dysplasia." *Pediatr. Infect Dis J* 17:787-91.
Saez Llorens et al., 1997. "Phase I/II open label multi dose escalation trial of a humanized respiratory syncytial virus (RSV) monoclonal antibody (Medi493) administered intramuscularly (IM) in high risk children." *Abstracts in Non HIV virology, ICAAC Toronto.*
Sahagan et al., 1986. "A genetically engineered murine/human chimeric antibody retains specificity for human tumor-associated antigen." *J. Immunol.* 137(3):1066-1074.
Sakurai et al., 1999. "Human antibody responses to mature and immature forms of viral envelope in respiratory syncytial virus infection: significance for subunit vaccines." *J Virol.* 73(4):2956-2962.
Saudek et al., 1989. "A Preliminary Trial of the Programmable Implantable Medication System for Insulin Delivery." *N Engl J Med.* 321(9):5749.
Schier et al., 1996. "Isolation of high-affinity monomeric human anticerbB2 single chain Fv using affinity-driven selection." *J. Mol. Biol.* 255(1):2843.
Schier et al., 1996. "Isolation of picomolar affinity anticerbB2 singlechain Fv by molecular evolution of the complementarity determining regions in the center of the antibody binding site." *J. Mol. Biol.* 263(4):551-567.
Scott et al., 1985. "Cellular reactivity to respiratory syncytial virus in human colostrum and breast milk." *J Med Virol.* 17(1):8393.
Seaver, 1994. "Monoclonal antibodies in industry: More difficult than originally thought" *Genetic Engineering News*, vol. 14, No. 14, p. 10 and 21.
Sefton, 1987. "Implantable Pumps." *CRC Crit. Rev. Biomed. Eng.* 14:201-240.
Sevier et al., 1981. "Monoclonal antibodies in clinical immunology." *Clin Chem.* 27(11):1797-806.
Shreder, 2000. "Synthetic haptens as probes of antibody response and immunorecognition" *Methods*; 20(3):372-9.
Sibille et al., 1997, "Mimotopes of polyreactive anti-DNA antibodies identified using hagedisplay peptide libraries", *Eur J Immunol*; 27: 1221-1228.
Skaricic et al., 2008, "Genetic delivery of an antiRSV antibody to protect against pulmonary infection with RSV," *Virology.* 378(1):7985.
Smith et al., 1991. "A Controlled Trial of Aerosolized Ribavirin in Infants Receiving Mechanical Ventilation for Severe Respiratory Syncytial Virus Infection," *N Engl J Med.* 325(1):249.
Song et al., 1995. "Antibody Mediated Lung Targeting of Long-Circulating Emulsions, PDA" *Journal of Pharmaceutical Science & Technology* 50: 372-77.
Sorbera et al., 1998. "Palivizumab." *Drug Data Report* 20:702-703.
Sorbera et al., 1998. "Palivizumab." *Drugs of the Future* 23:970-976.
Steplewski et al., 1988. "Biological activity of human-mouse IgG1, IgG2, IgG3, and IgG4 chimeric monoclonal antibodies with antitumor specificity." *Proc. Natl. Acad. Sci. USA* 85(13):4852-4856.
Stott et al., 1984. "The characterization and uses of monoclonal antibodies to respiratory syncytial virus." *Dev Biol Stand.* 57:237-44.
Studnicka et al., 1994. "Human-engineered monoclonal antibodies retain full specific binding activity by preserving non-CDR complementarity-modulating residues." *Protein Eng.* 7:805814.
Subramanian et al., 1997. "Randomized double blind placebo controlled dose escalation trial of a humanized respiratory syncytial virus monoclonal antibody in high risk infants." *Poster session infect. dis.* 130A:768.

Subramanian et al., 1998. "Safety, Tolerance and Pharmacokinetics of a Humanized Monoclonal Antibody to Respiratory Syncytial Virus in Premature Infants and Infants with Bronchopulmonary Dysplasia." *Pediatric Infect Dis J.* 17:110-115.
Sun et al., 1987. "Chimeric antibody with human constant regions and mouse variable regions directed against carcinoma-associated antigen 171A." *Proc. Natl. Acad. Sci. USA.* 84(1):214-218.
Takahashi et al. 1984. "Rearranged immunoglobulin heavy chain variable region (VH) pseudogene that deletes the second complementarity-determining region." *Proc. Natl. Acad. Sci. USA.* 81: 5194-198.
Takeda et al., 1985. "Construction of chimaeric processed immunoglobulin genes containing mouse variable and human constant region sequences." *Nature* 314(6010):452-454.
Talwar et al., 1976. "Isoimmunization against human chorionic gonadotropin with conjugates of processed beta-subunit of the hormone and tetanus toxoid," *Proc. Natl. Acad. Sci. USA.* 73(1):218-222.
Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000; 164:1432-1441.
Taylor et al., 1984. "Monoclonal antibodies protect against respiratory syncytial virus infection in mice." *Immunology.* 52(1):137-42.
Taylor et al., 1992. "Protective epitopes on the fusion protein of respiratory syncytial virus recognized by murine and bovine monoclonal antibodies." *J Gen Virol.* 73 ( Pt 9):2217-23.
The 65 years and older population: 2000: *Census 2000 Brief*, US Census Bureau.
The IMpactRSV Study Group, 1998. "Palivizumab, a humanized respiratory syncytial virus monoclonal antibody, reduces hospitalization from respiratory syncytial virus infection in high-risk infants." *Pediatrics.* 102(3 Pt 1):531-537.
Thompson et al., 1996. "Affinity maturation of a high-affinity human monoclonal antibody against the third hypervariable loop of human immunodeficiency virus: use of phage display to improve affinity and broaden strain reactivity." *J. Mol. Biol.* 256(1):77-88.
Trill et al., 1995, "Production of monoclonal antibodies in COS and CHO cells", *Curr Opin Biotechnol*;6(5):553-60.
U.S. Census Bureau "Age Data" 2000 Census http://www.census.gov/population/www/socdemo/age.html (last accessed Apr. 17, 2006).
U.S. Census Bureau, Age Data, website updated May 12, 2004, http://www.census.gov/population/www/socdemo/age.html.
U.S. Department of Commerce, Economies and Statistics Administration, Bureau of the Census, "We the American Elderly," Sep. 1993.
Van Der Merwe et al., 1993. "Affinity and kinetic analysis of the interaction of the cell adhesion molecules rat CD2 and CD48." *EMBO J.* 12(13):4945-4954.
Van Der Merwe et al., 1994. "Human cell-adhesion molecule CD2 binds CD58 (LFA3) with a very low affinity and an extremely fast dissociation rate but does not bind CD48 or CD59," *Biochemistry* 33(33):10149-10160.
Van Wyke Coelingh et al., 1985. "Antigenic variation in the hemagglutinin-neuraminidase protein of human parainfluenza type 3 virus." *Virology.* 143(2):569-582.
Vancott et al., 1994. "Dissociation rate of antibodygp120 binding interactions is predictive of V3mediated neutralization of HIV1." *J. Immunol.* 153(1):449-59.
Verma et al., 1997. "Gene therapy—promises, problems and prospects." *Nature.* 389:239-242.
Wald et al., 1988. "In re ribavirin: a case of premature adjudication?" *J. Pediatr.* 112(1):154-158.
Walsh et al., 1984. "Protection from respiratory syncytial virus infection in cotton rats by passive transfer of monoclonal antibodies." *Infect Immun.* 43(2):75-68.
Walsh et al., 1987. "Immunization with Glycoprotein Subunits of Respiratory Syncytial Virus to Protect Cotton Rats Against Viral Infection." *J Infect Dis.* 155(6):1198-204.

(56) References Cited

OTHER PUBLICATIONS

Ware et al., 1985. "Human, rat or mouse hybridomas secrete high levels of monoclonal antibodies following transplantation into mice with severe combined immunodeficiency disease (SCID)." *J. Immunol Methods*. 85(2):353-61.
Warren, 1990. "Salvage Receptors: Two of a Kind?" *Cell* 62:1-2.
Watkins et al., 1997. "Determination of the relative affinities of antibody fragments expressed in *Escherichia coli* by enzyme-linked immunosorbent assay." *Anal Biochem*. 253(1):37-45.
Watkins et al., 1998. "Discovery of human antibodies to cell surface antigens by capture lift screening of phage-expressed antibody libraries." *Anal Biochem*. 256(2):169-77.
Weltzin et al., 1989. "Binding and transepithelial transport of immunoglobulins by intestinal M cells: demonstration using monoclonal IgA antibodies against enteric viral proteins." *J Cell Biol*. 108(5): 1673-85.
Weltzin et al., 1994. "Intranasal Monoclonal Immunoglobulin A against Respiratory Syncytial Virus Protects against Upper and Lower Respiratory Tract Infections in Mice." *Antimicro Agents & Chemo*. 38(12):2785-2791.
Weltzin et al., 1996. "Intranasal Monoclonal IgA Antibody to Respiratory Syncytial Virus Protects Rhesus Monkeys against Upper and Lower Tract Infection." *J. of Infect Dis*. 174: 256-261.
Weltzin et al., 1999. "Intranasal antibody prophylaxis for protection against viral disease." *Clin Microbiol Rev*. 12(3):38393.
Whitlow et al., 1995. "1.85 A structure of antifluorescein 4420 Fab." *Protein Eng*. 8(8):749-761.
Wilson et al., 1984. "The structure of an antigenic determinant in a protein." *Cell*. 37(3):767-78.
Wright et al., 1982. "Administration of a highly attenuated, live respiratory syncytial virus vaccine to adults and children." *Infect. Immun*. 37(1):397-400.
Wu et al, 1999. "Humanization of murine monoclonal antibody by simultaneous optimization of framework and CDR residues." *J Mol Biol*. 294(1):151-62.
Wu et al., 2002. "Tailoring Kinetics of Antibodies Using Focused Combinatorial Libraries" chapter 13 from *Methods in Molecular Biology* vol. 207, Eds. Welschop and Krauss, Humana Press Inc., Totowa, NJ, pp. 213-233.
Wu et al., 1998. "Stepwise in vitro affinity maturation of Vitaxin, an avb-specitic humanized mAb." *Proc. Natl. Acad. Sci. USA*. 95:6037-6042.
Wu et al., 2005. "Ultrapotent Antibodies Against Respiratory Syncytial Virus: Effects of Binding Kinetics and binding Valence on Viral Neutralization." *J Mol Biol*. 350: 126-144.
Wu et al., 2007. "Development of Motavizumab, an Ultrapotent Antibody for the Prevention of Respiratory Syncytial Virus Infection in the Upper and Lower Respiratory Track." *J Mol Biol*. 368(3): 652-65.
Wu et al., 2008. "Immunoprophylaxis of RSV Infection: Advancing from RSVIGIV to Palivizumab and Motavizumab," *Curr Topics Microbiol Immunol*. 317:103-123.
Wyde et al., 1995 "Evaluation of the protective efficacy of reshaped human monoclonal antibody RSHZ19 against respiratory syncytial virus in cotton rats," *Pediatr Res*, 38(4):543-50.
Yang et al., 1995. "CDR walking mutagenesis for the affinity maturation of a potent human anitHIV1 antibody into the picomolar range." *J Mol Biol*. 254:392-403.
U.S. Appl. No. 09/724,396; Office Action dated Mar. 26, 2002.
U.S. Appl. No. 09/724,396; Office Action dated Apr. 5, 2004.
U.S. Appl. No. 09/724,396; Office Action dated Jun. 3, 2003.
U.S. Appl. No. 09/724,396; Office Action dated Jul. 28, 2003.
U.S. Appl. No. 09/724,396; Office Action dated Dec. 3, 2002.
U.S. Appl. No. 09/724,531 (now U.S. Pat. No. 7,229,619); Office Action / Notice of Allowance dated Jan. 30, 2007.
U.S. Appl. No. 09/724,531 (now U.S. Pat. No. 7,229,619); Office Action / Notice of Allowance dated Aug. 22, 2006.
U.S. Appl. No. 09/724,531 (now U.S. Pat. No. 7,229,619); Office Action dated Feb. 9, 2005.
U.S. Appl. No. 09/724,531 (now U.S. Pat. No. 7,229,619); Office Action dated Feb. 21, 2003.
U.S. Appl. No. 09/724,531 (now U.S. Pat. No. 7,229,619); Office Action dated Apr. 4, 2006.
U.S. Appl. No. 09/724,531 (now U.S. Pat. No. 7,229,619); Office Action dated Jun. 4, 2004.
U.S. Appl. No. 09/724,531 (now U.S. Pat. No. 7,229,619); Office Action dated Jun. 15, 2005.
U.S. Appl. No. 09/724,531 (now U.S. Pat. No. 7,229,619); Office Action dated Oct. 21, 2003.
U.S. Appl. No. 09/771,415 (now U.S. Pat. No. 6,656,467); Office Action / Notice of Allowability dated May 6, 2003.
U.S. Appl. No. 09/771,415 (now U.S. Pat. No. 6,656,467); Office Action dated Feb. 10, 2003.
U.S. Appl. No. 09/771,415 (now U.S. Pat. No. 6,656,467); Office Action dated Jun. 18, 2002.
U.S. Appl. No. 09/796,848 (now U.S. Pat. No. 7,700,735); Office Action / Notice of Allowance dated Nov. 16, 2009.
U.S. Appl. No. 09/796,848 (now U.S. Pat. No. 7,700,735); Office Action dated Jan. 22, 2009.
U.S. Appl. No. 09/796,848 (now U.S. Pat. No. 7,700,735); Office Action dated Apr. 4, 2006.
U.S. Appl. No. 09/796,848 (now U.S. Pat. No. 7,700,735); Office Action dated Apr. 14, 2008.
U.S. Appl. No. 09/796,848 (now U.S. Pat. No. 7,700,735); Office Action dated Jun. 18, 2002.
U.S. Appl. No. 09/796,848 (now U.S. Pat. No. 7,700,735); Office Action dated Jul. 13, 2005.
U.S. Appl. No. 09/796,848 (now U.S. Pat. No. 7,700,735); Office Action dated Jul. 27, 2007.
U.S. Appl. No. 09/796,848 (now U.S. Pat. No. 7,700,735); Office Action dated Oct. 29, 2004.
U.S. Appl. No. 09/796,848 (now U.S. Pat. No. 7,700,735); Office Action dated Dec. 29, 2003.
U.S. Appl. No. 09/996,265 (now U.S. Pat. No. 6,855,493); Office Action / Notice of Allowability dated Mar. 31, 2004.
U.S. Appl. No. 09/996,265 (now U.S. Pat. No. 6,855,493); Office Action / Supplemental Notice of Allowability dated Jul. 13, 2004.
U.S. Appl. No. 09/996,265 (now U.S. Pat. No. 6,855,493); Office Action dated Aug. 12, 2003.
U.S. Appl. No. 09/996,288 (now U.S. Pat. No. 6,818,216); Office Action / Notice of Allowability dated Jan. 29, 2004.
U.S. Appl. No. 09/996,288 (now U.S. Pat. No. 6,818,216); Office Action / Notice of Allowability dated Jun. 30, 2004.
U.S. Appl. No. 09/996,288 (now U.S. Pat. No. 6,818,216); Office Action / Supplemental Notice of Allowability dated Jul. 28, 2004.
U.S. Appl. No. 09/996,288 (now U.S. Pat. No. 6,818,216); Office Action dated Jul. 14, 2003.
U.S. Appl. No. 10/020,354 (now U.S. Pat. No. 7,083,784); Office Action / Notice of Allowability dated Dec. 15, 2005.
U.S. Appl. No. 10/020,354 (now U.S. Pat. No. 7,083,784); Office Action dated Apr. 7, 2004.
U.S. Appl. No. 10/020,354 (now U.S. Pat. No. 7,083,784); Office Action dated Jun. 1, 2005.
U.S. Appl. No. 10/020,354 (now U.S. Pat. No. 7,083,784); Office Action dated Nov. 17, 2004.
U.S. Appl. No. 10/403,180 (now U.S. Pat. No. 7,179,900); Office Action / Notice of Allowability dated Sep. 6, 2006.
U.S. Appl. No. 10/403,180 (now U.S. Pat. No. 7,179,900); Office Action dated Mar. 30, 2006.
U.S. Appl. No. 10/403,180 (now U.S. Pat. No. 7,179,900); Office Action dated Apr. 4, 2005.
U.S. Appl. No. 10/403,180 (now U.S. Pat. No. 7,179,900); Office Action dated Oct. 19, 2005.
U.S. Appl. No. 10/461,863 (now U.S. Pat. No. 7,425,618); Office Action / Notice of Allowability dated Nov. 19, 2007.
U.S. Appl. No. 10/461,863 (now U.S. Pat. No. 7,425,618); Office Action dated Jun. 11, 2007.
U.S. Appl. No. 10/461,863 (now U.S. Pat. No. 7,425,618); Office Action dated Dec. 18, 2006.
U.S. Appl. No. 10/461,863 (now U.S. Pat. No. 7,425,618); Supplemental Notice of Allowability dated Jul. 31, 2008.

(56) References Cited

OTHER PUBLICATIONS

U.S. Appl. No. 10/461,904 (now U.S. Pat. No. 7,132,100); Office Action / Notice of Allowability dated May 2, 2006.
U.S. Appl. No. 10/461,904 (now U.S. Pat. No. 7,132,100); Office Action / Notice of Allowability dated Nov. 25, 2005.
U.S. Appl. No. 10/461,904 (now U.S. Pat. No. 7,132,100); Office Action dated Dec. 14, 2004.
U.S. Appl. No. 10/657,363; Interview Summary Oct. 8, 2009.
U.S. Appl. No. 10/657,363 (U.S. Publ. No. 2004/0131609); Office Action / Notice of Allowability dated Dec. 31, 2008.
U.S. Appl. No. 10/657,363 (U.S. Publ. No. 2004/0131609); Office Action / Notice of Allowability dated Feb. 4, 2010.
U.S. Appl. No. 10/657,363 (U.S. Publ. No. 2004/0131609); Office Action dated May 30, 2007.
U.S. Appl. No. 10/657,363 (U.S. Publ. No. 2004/0131609); Office Action dated Jul. 6, 2009.
U.S. Appl. No. 10/657,363 (now U.S. Publ. No. 2004/0131609); Office Action dated Dec. 14, 2007.
U.S. Appl. No. 10/900,230 (now U.S. Pat. No. 7,635,568); Interview Summary dated Mar. 27, 2009.
U.S. Appl. No. 10/900,230 (now U.S. Pat. No. 7,635,568); Office Action / Notice of Allowance dated Jun. 17, 2009.
U.S. Appl. No. 10/900,230 (now U.S. Pat. No. 7,635,568); Office Action / Notice of Allowance dated Jun. 27, 2007.
U.S. Appl. No. 10/900,230 (now U.S. Pat. No. 7,635,568); Office Action dated Jan. 24, 2006.
U.S. Appl. No. 10/900,230 (now U.S. Pat. No. 7,635,568); Office Action dated Feb. 21, 2008.
U.S. Appl. No. 10/900,230 (now U.S. Pat. No. 7,635,568); Office Action dated Jun. 30, 2006.
U.S. Appl. No. 10/900,230 (now U.S. Pat. No. 7,635,568); Office Action dated Sep. 18, 2008.
U.S. Appl. No. 10/900,230 (now U.S. Pat. No. 7,635,568); Office Action dated Dec. 26, 2006.
U.S. Appl. No. 10/962,285 (now U.S. Pat. No. 7,323,172); Office Action / Notice of Allowability dated Sep. 6, 2007.
U.S. Appl. No. 10/962,285 (now U.S. Pat. No. 7,323,172); Office Action dated Apr. 13, 2007.
U.S. Appl. No. 10/962,285 (now U.S. Pat. No. 7,323,172); Office Action dated Oct. 26, 2006.
U.S. Appl. No. 11/263,230 (U.S. Publ. No. 2006/0115485); Office Action dated Jan. 9, 2008.
U.S. Appl. No. 11/263,230 (U.S. Publ. No. 2006/0115485); Office Action dated Mar. 30, 2009.
U.S. Appl. No. 11/263,230 (U.S. Publ. No. 2006/0115485); Office Action dated Oct. 2, 2008.
U.S. Appl. No. 11/362,267 (now U.S. Pat. No. 7,294,336); Office Action / Notice of Allowability dated Aug. 6, 2007.
U.S. Appl. No. 11/362,267 (now U.S. Pat. No. 7,294,336); Office Action dated May 4, 2007.
U.S. Appl. No. 11/397,328 (now U.S. Pat. No. 7,670,600); Office Action / Notice of Allowability dated Aug. 7, 2008.
U.S. Appl. No. 11/397,328 (now U.S. Pat. No. 7,670,600); Office Action dated Feb. 13, 2009.
U.S. Appl. No. 11/397,328 (now U.S. Pat. No. 7,670,600); Office Action dated Oct. 18, 2007.
U.S. Appl. No. 11/397,328 (now U.S. Pat. No. 7,670,600); Issue Fee Payment for dated Dec. 23, 2009.
U.S. Appl. No. 11/397,328 (now U.S. Pat. No. 7,670,600); Notice of Allowance and Fees due dated Sep. 29, 2009.
U.S. Appl. No. 11/643,982 (now U.S. Pat. No. 7,553,489); Office Action / Notice of Allowability dated Feb. 13, 2009.
U.S. Appl. No. 11/643,982 (now U.S. Pat. No. 7,553,489); Office Action dated Sep. 2, 2008.
U.S. Appl. No. 11/649,455 (now U.S. Pat. No. 7,704,497); Office Action dated Feb. 26, 2009.
U.S. Appl. No. 11/649,455 (now U.S. Pat. No. 7,704,497); Notice of Allowance and Fees due dated Nov. 24, 2009.
U.S. Appl. No. 11/906,543 (now U.S. Pat. No. 7,785,592); Office Action / Notice of allowability dated Mar. 16, 2010.
U.S. Appl. No. 11/906,543 (now U.S. Pat. No. 7,785,592); Office Action dated Jun. 12, 2009.
U.S. Appl. No. 11/906,543 (now U.S. Pat. No. 7,785,592); Office Action dated Apr. 7, 2009.
U.S. Appl. No. 11/906,543 (now U.S. Pat. No. 7,785,592); Office Action dated Oct. 19, 2009.
U.S. Appl. No. 12/075,197 (U.S. Publ. No. 2009/0175883); Office Action / Interview Summary dated Jul. 22, 2010.
U.S. Appl. No. 12/075,197 (U.S. Publ. No. 2009/0175883); Office Action dated Mar. 26, 2010.
U.S. Appl. No. 12/075,197 (U.S. Publ. No. 2009/0175883); Office Action dated Nov. 16, 2010.
U.S. Appl. No. 12/075,197 (U.S. Publ. No. 2009/0175883); Office Action dated Apr. 28, 2011.
U.S. Appl. No. 12/476,183; Notice of Allowance and Fees due dated Jul. 14, 2010.
U.S. Appl. No. 12/559,375 (U.S. Publ. No. 2010/0098708); Office Action dated Jun. 17, 2010.
U.S. Appl. No. 12/691,433 (now U.S. Pat. No. 8,012,476); Notice of Allowability dated Apr. 28, 2011.
U.S. Appl. No. 12/691,433 (now U.S. Pat. No. 8,012,476); Office Action dated Nov. 5, 2010.
U.S. Appl. No. 12/707,527 (now U.S. Pat. No. 8,153,133); Notice of Allowability dated Dec. 2, 2011.
U.S. Appl. No. 12/707,527 (now U.S. Pat. No. 8,153,133); Office Action dated Feb. 25, 2011.
U.S. Appl. No. 12/707,527 (now U.S. Pat. No. 8,153,133); Office Action dated Jul. 29, 2011.
U.S. Appl. No. 12/707,527 (now U.S. Pat. No. 8,153,133); Office Action dated Dec. 9, 2010.
U.S. Appl. No. 12/777,814 (U.S. Publ. No. 2010/0266614); Office Action dated Jun. 24, 2011.
U.S. Appl. No. 12/777,814; Office Action dated Nov. 12, 2010.
U.S. Appl. No. 12/817,097 (now U.S. Pat. No. 8,007,793); Notice of Allowability dated Apr. 18, 2011.
U.S. Appl. No. 12/817,097 (now U.S. Pat. No. 8,007,793); Office Action dated Dec. 1, 2010.
U.S. Appl. No. 12/969,514 (now U.S. Publ. No. 2011/0158985); Office Action dated Dec. 15, 2011.
U.S. Appl. No. 13/184,455 (U.S. Publ. No. 2012/0039876); Notice of Allowability dated Mar. 1, 2012.
U.S. Appl. No. 12/600,950 (U.S. Publ. No. 2010/239593); Office Action dated Feb. 2, 2012.
U.S. Appl. No. 12/600,950 (U.S. Publ. No. 2010/239593); Office Action dated Jun. 12, 2012.
International Search Report of International application No. PCT/NL2009/050599, dated Jun. 15, 2010.
Written Opinion of International application No. PCT/NL2009/050599, dated Jun. 15, 2010.

\* cited by examiner

RSV nAb AM22 clone

NB: CDR numbering according to Kabat et al (1991)

<u>Heavy chain</u>

Recombined from gene segments:
IGHV1-24*01
IGHD6-19*01
IGHJ4*02

AMINO ACID:

Fw1 QVQLVQSGAEVKKPGATVKVSCKISGHTLT (SEQ ID NO. 2)

CDR1 KLSIH (SEQ ID NO. 4)

Fw2 WVRQAPGKGLEWMG (SEQ ID NO. 6)

CDR2 GYEGEVDEIFYAQKFQH (SEQ ID NO. 8)

Fw3 RLTVIADTATDTVYMELGRLTSDDTAVYFCGT (SEQ ID NO. 10)

CDR3 LGVTVTEAGLGIDDY (SEQ ID NO. 12)

Fw4 WGQGTLVTVSS (SEQ ID NO. 14)

NUCLEOTIDE:
Fw1 cag gtc cag ctg gta cag tct ggg gct gag gtg aag aag ccc ggg gcc aca gtg aaa gtc tcc tgc aag att tcc gga cac acc ctc att (SEQ ID NO. 1)

CDR1 aaa tta tcc att cac (SEQ ID NO. 3)

Fw2 tgg gtg cga cag gct cct gga aag ggg ctt gag tgg atg gga (SEQ ID NO. 5)

CDR2 ggt tat gag ggt gag gtc gat gag att ttc tac gca cag aag ttc cag cac (SEQ ID NO. 7)

Fw3 aga ctc acc gtg atc gcc gac aca gcg aca gac aca gtc tac atg gaa ctg ggc agg ctc acc tct gac gac acg gcc gtc tat ttc tgt gga aca (SEQ ID NO. 9)

CDR3 cta ggt gtg aca gtg act gag gct gga ctg ggg atc gat gac tac (SEQ ID NO. 11)

Fw4 tgg ggc cag gga acc ctg gtc acc gtc tcc tca (SEQ ID NO. 13)

Figure 2A

Light chain

Recombined from gene segments:
IGKV3-20*02
IGKJ3*01

AMINO ACID:

FW1 EIVLTQSPGTLSLSPGERATLSC (SEQ ID NO. 18)

CDR1 RASQIVSNNLA (SEQ ID NO. 20)

FW2 WYQQKPGQAPRLLIF (SEQ ID NO. 22)

CDR2 GASSRAT (SEQ ID NO. 24)

FW3 GIPVRFSGSGSGTDFTLTISGLAPEDFAVYYC (SEQ ID NO. 26)

CDR3 LSSDSSI (SEQ ID NO. 28)

FW4 FTFGPGTKVDFK (SEQ ID NO. 30)

NUCLEOTIDE:
FW1 gaa att gtg ttg aca cag tct cca ggc acc ctg tct ttg tct cca gga gaa aga gcc acc ctc tcc tgc (SEQ ID NO. 17)

CDR1 agg gcc agt cag att gtt agc agg aac tac tta gcc (SEQ ID NO. 19)

FW2 tgg tac cag caa aaa cct ggc cag gct ccc agg ctc ctc atc ttt (SEQ ID NO. 21)

CDR2 ggt gcg tcc agt cgg gcc act (SEQ ID NO. 23)

FW3 ggc atc cca gtc agg ttc agt ggc agt ggg tct ggg aca gac ttc act ctc acc atc aac gga ctg gcg cct gaa gat ttt gca gtt tac tac tgt (SEQ ID NO. 25)

CDR3 ctg tcc tct gat tcc tcc ata (SEQ ID NO. 27)

FW4 ttc acg ttc ggc cct ggg acc aag gtg gat ttc aaa (SEQ ID NO. 29)

Figure 2B

RSV-SPECIFIC BINDING MOLECULE

This application is a continuation patent application of U.S. patent application Ser. No. 15/042,656, filed on Feb. 12, 2016, which is a continuation patent application of U.S. patent application Ser. No. 14/039,148, filed on Sep. 27, 2013, which is a continuation patent application of U.S. patent application Ser. No. 12/898,325, filed on Oct. 5, 2010, which claims priority to U.S. Provisional Patent Application No. 61/278,358, filed Oct. 6, 2009, each of which is incorporated herein by reference.

SEQUENCE LISTING

This application contains a Sequence Listing electronically submitted to the United States Patent and Trademark Office via EFS-Web as an ASCII text file entitled "490-00020104_SequenceListing_ST25.txt" having a size of 16 kilobytes and created on Jul. 26, 2018. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

The Invention Relates to the Fields of Biology and Medicine

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4500 deaths per year were reported in United States. Major risk factors for hospitalization due to RSV are premature birth, chronic lung disease, congenital heart disease, compromised immunity, and age younger than 6 weeks in otherwise healthy children. No effective treatment of RSV positive bronchiolitis beside supportive care in the form of adequate nutrition and oxygen therapy is available. Antiviral therapies such as Ribavirin have not been proven to be effective in RSV infection. One monoclonal antibody, palivizumab (also called Synagis), is registered for prophylaxis against RSV infection. Palivizumab is a genetically engineered (humanized) monoclonal antibody to the fusion protein (F protein) of RSV. The F protein of RSV is a viral membrane protein and responsible for fusion of the virion with a host cell after attachment. In addition, infection of neighboring cells through the formation of syncytia is promoted by the F protein and its function is thought to depend on the original oligomeric structure of the protein. However, palivizumab is not always effective. Therefore, there is a need in the art for alternative and/or supplementary antibodies and therapies against RSV.

It is an object of the invention to provide improved antibodies against RSV, or functional equivalents of such antibodies. It is a further object to provide supplementary antibodies against RSV, which, in combination with existing RSV-specific antibodies, provide a synergistic effect. It is a further object of the invention to provide human or humanized antibodies or functional equivalents against the RSV F protein which are directed against an epitope that is different from the epitopes that known RSV-specific antibodies are directed against.

Accordingly, the present invention provides an isolated, synthetic or recombinant antibody or a functional part, derivative and/or analogue thereof which is capable of specifically binding Respiratory Syncytial Virus and which comprises:

a heavy chain CDR1 sequence comprising a sequence which is at least 70% identical to the sequence KLSIH (SEQ ID NO:4), and/or a heavy chain CDR2 sequence comprising a sequence which is at least 70% identical to the sequence GYEGEVDEIFYAQKFQH (SEQ ID NO:8), and/or a heavy chain CDR3 sequence comprising a sequence which is at least 70% identical to the sequence LGVTVTEAGLGIDDY (SEQ ID NO:12), and/or a light chain CDR1 sequence comprising a sequence which is at least 70% identical to the sequence RASQIVSRNHLA (SEQ ID NO:20), and/or a light chain CDR2 sequence comprising a sequence which is at least 70% identical to the sequence GASSRAT (SEQ ID NO:24), and/or a light chain CDR3 sequence comprising a sequence which is at least 70% identical to the sequence LSSDSSI (SEQ ID NO:28).

The present invention provides an antibody designated "AM22", which has heavy chain and light chain sequences as depicted in FIG. 2. The CDR sequences of AM22, which in particular contribute to the antigen-binding properties of AM22, are also depicted in FIG. 2. Antibody AM22 is fully human, is capable of specifically binding RSV (FIG. 3) and is therefore preferred for prophylactic and/or therapeutic use for human individuals.

As mentioned above the only available clinically used anti-RSV antibody is palivizumab. This is a humanized monoclonal antibody directed against an epitope in the antigenic site of the F protein of RSV. Humanized antibodies still contain part of a mouse antibody and although immunogenic properties are diminished as compared to fully mouse antibodies, side-effects of humanized antibodies may occur when applied in humans. The present inventors, however, succeeded in obtaining and culturing human B-cells producing RSV-specific antibodies, so that human RSV-specific antibodies have been provided, that have strongly reduced—if at all—immunogenic activity as a result of the completely human sequence. As shown in the examples, antibodies according to the invention have superior characteristics as compared to palivizumab (FIG. 1 and table 1). The present inventors have shown that Cotton rats (*Sigmodon hispidus*) given antibodies according to the invention by intramuscular injection followed by intranasal challenge with RSV-X have a lower Pathology Index than Cotton rats given palivizumab followed by challenge with RSV-X (FIG. 4C and table 2). The Pathology Index used herein is a sum of scores to classify three individual markers for lung damage. These three markers are hyperthropy of bronchus and bronchioli epithelium, inflammation surrounding bronchus and bronchioli (peribronch(iol)itis) and inflammation in the alveoli (alveolitis). In addition, Cotton rats injected intramuscularly with antibodies according to the invention and subsequent RSV-X challenge had lower lung virus titers than Cotton rats given palivizumab followed by challenge with RSV-X (FIG. 4B), which was determined by TCID50 (50% tissue culture infective dose) assay. Hence, AM22 is preferred over palivizumab.

Besides palivizumab, some other RSV-specific antibodies are known. WO 2008/147196 discloses sequences of RSV binding molecules, namely antibodies D25, AM14, AM16 and AM23. As described in detail in example 1 of the current application, RSV specific antibody AM22 was obtained from the same donor as antibodies D25, AM14, AM16 and AM23. Strikingly however, AM22 recognizes RSV more efficiently than all other antibodies obtained from the same donor. The $IC_{50}$ value of AM22, 1.15 ng ml$^{-1}$, is lower than that of palivizumab, D25, AM14, AM16 or AM23. Therefore, the use of AM22 for treatment and/or prevention of a RSV-related disorder has advantages over the use of other RSV specific antibodies. Less AM22 antibody is necessary to obtain a similar effect compared to the other antibodies. Therefore, less AM22 has to be administered to an individual for treatment and/or prevention of a RSV-related disorder. Alternatively, with a similar amount of AM22, as compared to the other antibodies, a more effective treatment and/or prevention of a RSV-related disorder is achieved.

Furthermore, an RSV-specific antibody according to the present invention recognizes a different epitope as the previously disclosed RSV binding molecules. AM22, similar to the previously identified antibodies (WO2008/147196), is capable of binding the RSV F protein (FIG. 3A). However, AM22 does not bind a monomeric RSV F protein (FIG. 3B left and right panel). Contrary to AM22, the known antibodies palivizumab and AM16 (disclosed in WO 2008/147196 and FIG. 3B) are capable of binding the monomeric form of the F protein. Importantly the AM22 B cell line, expressing the antigen specific B Cell Receptor (BCR) does not recognize a recombinant form of the F protein (FIG. 3C). Thus AM22 binds a different epitope of the F protein than palivizumab, D25, AM23 and AM16. When the recombinant F protein was expressed in a vector containing an isoleucine zipper trimerization motif with eight HIS-tags (ILZ-8×HIS), then AM22 recognized this trimeric, conformation dependent structure (FIG. 3D). In contrast AM14 did not recognize either the monomeric form of the F protein or the ILZ-8×HIS F protein. Thus AM22 binds a different epitope of the F protein than AM14 as well. Furthermore it was found that AM22 did not interfere with D25 or palivizumab binding to RSV infected Hep2 cells. Thus, AM22 binds a different epitope of the F protein as compared to D25, AM14, AM16, AM23 and palivizumab. Therefore, RSV-specific antibodies or functional equivalents thereof according to the present invention are preferably combined with RSV-specific antibodies that are already known, such as palivizumab, D25, AM14, AM16 and AM23. By combining an antibody according to the invention with a known RSV-specific antibody, two or more different epitopes of RSV are recognized during the same therapy. This way, a stronger immunogenic response to RSV is obtained. Furthermore, higher antibody specificity against RSV is reached by combining one of the known RSV-specific antibodies with an AM22 antibody according to the invention. With a stronger immunogenic response to and higher specificity against RSV, such combination will result in more effective treatment and/or prevention of a RSV-related disorder. Finally, a lower overall antibody dosage is needed because AM22 has a stronger binding capacity for the F protein compared to palivizumab, D25, AM14, AM16 and AM23, as demonstrated by its low $IC_{50}$ value, of about 1.15 ng/ml.

One embodiment therefore provides an antibody or functional equivalent according to the invention which has an $IC_{50}$ value less than 1.25 ng/ml in an in vitro neutralization assay wherein HEp-2 cells are infected with RSV-A2 virus. Said antibody or functional equivalent preferably has an $IC_{50}$ value of less than 1.2 ng/ml, preferably between 0.5 ng/ml and 1.2 ng/ml. Additionally, an antibody or functional equivalent according to the invention preferably has an $IC_{50}$ value which is at least 120-fold lower, more preferably at least 130-fold lower, than the $IC_{50}$ value of palivizumab in an in vitro neutralization assay wherein HEp-2 cells are infected with RSV-A2 virus. Said antibody or functional equivalent preferably has an $IC_{50}$ value of about 1.15 ng/ml. Thus with an RSV-specific antibody or functional equivalent thereof according to the present invention in combination with at least one available RSV-specific antibody a more effective treatment and/or prevention of a RSV-related disorder is achieved.

A functional equivalent of an antibody is defined herein as a functional part, derivative or analogue of an antibody. A functional equivalent of an antibody is preferably an artificial binding compound, comprising at least one CDR sequence of an antibody.

A functional part of an antibody is defined as a part which has at least one same property as said antibody in kind, not necessarily in amount. Said functional part is capable of binding the same antigen as said antibody, albeit not necessarily to the same extent. A functional part of an antibody preferably comprises a single domain antibody, a single chain antibody, a single chain variable fragment (scFv), a Fab fragment or a F(ab')$_2$ fragment.

A functional derivative of an antibody is defined as an antibody which has been altered such that at least one property—preferably an antigen-binding property—of the resulting compound is essentially the same in kind, not necessarily in amount. A derivative is provided in many ways, for instance through conservative amino acid substitution, whereby an amino acid residue is substituted by another residue with generally similar properties (size, hydrophobicity, etc), such that the overall functioning is likely not to be seriously affected.

A person skilled in the art is well able to generate analogous compounds of an antibody. This is for instance done using a peptide library or phage display library. Such an analogue has essentially at least one same property as said antibody in kind, not necessarily in amount.

An antibody according to the invention is preferably a human antibody. The use of human antibodies for prophylaxis and therapy in humans diminishes the chance of side-effects due to an immunological reaction in a human individual against non-human sequences. In another embodiment an antibody, functional part, derivative or analogue according to the invention is a humanized antibody. Humanized antibodies are made by incorporating non-human hypervariable domains into human antibodies and therefore immunogenic properties are diminished as compared to fully non-human antibodies. In another preferred embodiment an antibody or functional part, derivative or analogue according to the invention is a chimeric antibody. This way, sequences of interest, such as for instance a binding site of interest, can be included into an antibody or functional equivalent according to the invention.

As is well known by the skilled person, a heavy chain of an antibody is the larger of the two types of chains making up an immunoglobulin molecule. A heavy chain comprises constant domains and a variable domain, which variable domain is involved in antigen binding. A light chain of an antibody is the smaller of the two types of chains making up an immunoglobulin molecule. A light chain comprises a constant domain and a variable domain. The variable domain is, together with the variable domain of the heavy chain, involved in antigen binding.

Complementary-determining regions (CDRs) are the hypervariable regions present in heavy chain variable domains and light chain variable domains. The CDRs of a heavy chain and the connected light chain of an antibody together form the antigen-binding site.

Now that the present invention provides the insight that the CDR sequences depicted in FIG. 2 provide desired binding characteristics, a skilled person is well capable of generating variants comprising at least one altered CDR sequence. For instance, conservative amino acid substitution is applied. It is also possible to alter at least one CDR sequence depicted in FIG. 2 in order to generate a variant antibody, or a functional equivalent thereof, with at least one altered property as compared to AM22. Preferably, an antibody or functional equivalent is provided comprising a CDR sequence which is at least 70% identical to a CDR sequence as depicted in FIG. 2, so that the favorable binding characteristics of AM22 are at least in part maintained or even improved. A CDR sequence as depicted in FIG. 2 is preferably altered such that the resulting antibody or functional equivalent/comprises at least one improved property, such as for instance an improved stability and/or binding affinity, as compared to AM22. The binding specificity is preferably maintained (in kind, not necessarily in amount). Variant antibodies or functional equivalents thereof comprising an amino acid sequence which is at least 70% identical to a CDR sequence as depicted in FIG. 2 are therefore also within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed—mutagenesis.

Measurement of the affinity constant and specificity of binding between antigen and antibody is preferred in determining the efficacy of prophylactic, therapeutic, diagnostic and research methods using anti-RSV antibodies of the invention. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the equilibrium dissociation constant (Kd), which is calculated as the ratio $k_{off}/k_{on}$. See, e.g., Chen, Y., et al., (1999) *J. Mol Biol* 293:865-881. Affinity can be measured by common methods known in the art, such as for instance a surface plasmon resonance (SPR) assay such as BiaCore or IBIS-iSPR instrument at IBIS Technologies BV (Hengelo, the Netherlands) or solution phase assays, such as Kinexa.

According to preferred embodiments, the present anti-RSV antibodies of the invention have binding affinities for an epitope on the RSV F protein that include a dissociation constant ($K_d$) of less than $1\times10^{-2}$M, $1\times10^{-3}$M, $1\times10^{-4}$M, $1\times10^{-5}$M, $1\times10^{-6}$M, $1\times10^{-7}$M, $1\times10^{-8}$M, $1\times10^{-9}$M, $1\times10^{-10}$M, $1\times10^{-11}$M, $1\times10^{-12}$M, $1\times10^{-13}$M, $1\times10^{-14}$M or less than $1\times10^{-15}$M. In one embodiment, the anti-RSV antibodies have a $K_d$ of less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M.

The invention further provides an isolated, synthetic or recombinant antibody or a functional part, derivative and/or analogue thereof, which comprises:

a heavy chain CDR1 sequence comprising a sequence which has at least 70% sequence identity to the sequence KLSIH (SEQ ID NO: 4), and/or
a heavy chain CDR2 sequence comprising a sequence which has at least 70% sequence identity to the sequence GYEGEVDEIFYAQKFQH (SEQ ID NO: 8), and/or
a heavy chain CDR3 sequence comprising a sequence which has at least 70% sequence identity to the sequence LGVTVTEAGLGIDDY (SEQ ID NO: 12) and/or
a light chain CDR1 sequence comprising a sequence which is at least 70% identical to the sequence RASQIVSRNHLA (SEQ ID NO: 20), and/or
a light chain CDR2 sequence comprising a sequence which is at least 70% identical to the sequence GASSRAT (SEQ ID NO: 24), and/or
a light chain CDR3 sequence comprising a sequence which is at least 70% identical to the sequence LSSDSSI (SEQ ID NO: 28).

Preferably, an antibody or functional equivalent according to the invention comprises a CDR sequence which is at least 75%, more preferably at least 80%, more preferably at least 85%, more preferably at least 90% identical to at least one of the CDR sequences depicted in FIG. 2. Most preferably, an antibody or functional equivalent according to the invention comprises a CDR sequence which is at least 95% identical to at least one of the CDR sequences depicted in FIG. 2. The particularly preferred antibody AM22, described above, comprises CDR sequences which consist of the CDR sequences depicted in FIG. 2. A particularly preferred embodiment according to the invention thus provides an isolated, synthetic or recombinant antibody or a functional equivalent thereof which is capable of specifically binding RSV and which comprises:

a heavy chain CDR1 sequence comprising the sequence KLSIH (SEQ ID NO: 4), and/or
a heavy chain CDR2 sequence comprising the sequence GYEGEVDEIFYAQKFQH (SEQ ID NO: 8), and/or
a heavy chain CDR3 sequence comprising the sequence LGVTVTEAGLGIDDY (SEQ ID NO: 12), and/or
a light chain CDR1 sequence comprising the sequence RASQIVSRNHLA (SEQ ID NO: 20), and/or
a light chain CDR2 sequence comprising the sequence GASSRAT (SEQ ID NO: 24), and/or
a light chain CDR3 sequence comprising the sequence LSSDSSI (SEQ ID NO: 28).

In one embodiment an antibody or functional equivalent is provided which comprises the heavy chain CDR1 and CDR2 sequences and the light chain CDR1 and CDR2 sequences as depicted in FIG. 2, or sequences that are at least 70%, preferably at least 75%, more preferably at least 80%, more preferably at least 85% identical thereto. Further provided is therefore an isolated, synthetic or recombinant antibody or a functional part, derivative and/or analogue thereof which comprises a heavy chain CDR1 sequence comprising a sequence which is at least 70% identical to the sequence KLSIH (SEQ ID NO: 4) and a heavy chain CDR2 sequence comprising a sequence which is at least 70% identical to the sequence GYEGEVDEIFYAQKFQH (SEQ ID NO: 8) and a light chain CDR1 sequence comprising a sequence which is at least 70% identical to the sequence RASQIVSRNHLA (SEQ ID NO: 20) and a light chain CDR2 sequence comprising a sequence which is at least 70% identical to the sequence GASSRAT (SEQ ID NO: 24). Said antibody or functional equivalent preferably comprises CDR sequences which are at least 75%, more preferably at least 80%, more preferably at least 85%, more preferably at least 90%, most preferably at least 95% identical to the above mentioned heavy chain CDR sequences and light chain CDR sequences. Preferably, said antibody or functional equivalent also comprises a heavy chain CDR3 sequence comprising a sequence which is at least 70% identical to the sequence LGVTVTEAGLGIDDY (SEQ ID NO: 12), and/or a light chain CDR3 sequence comprising a sequence which is at least 70% identical to the sequence LSSDSSI (SEQ ID NO: 28). An antibody or functional equivalent comprising the above mentioned heavy chain CDR1, CDR2 and CDR3 sequences as well as the above mentioned light chain CDR1, CDR2 and CDR3 sequences is also provided.

Optionally, said at least one human CDR sequence is optimized, preferably in order to improve binding efficacy or stability. This is for instance done by mutagenesis experiments where after the stability and/or binding efficacy of the resulting compounds are preferably tested and an improved antibody or functional equivalent is selected.

Besides optimizing CDR sequences, it is often advantageous to optimize at least one sequence in at least one of the frame work regions. This is preferably done in order to improve binding efficacy or stability. Frame work sequences are for instance optimized by mutating a nucleic acid molecule encoding such frame work sequence where after the characteristics of the resulting antibody—or functional part—is preferably tested. This way, it is possible to obtain improved antibodies or functional parts. Isolated, synthetic or recombinant antibodies or functional parts, derivatives and/or analogues thereof comprising a heavy chain amino acid sequence which has at least 70% sequence identity to the heavy chain sequence as depicted in FIG. 2 are therefore also provided. Such heavy chain sequence provides desired binding properties, as evidenced by antibody AM22. Moreover, light chain amino acid sequences which have at least 70% sequence identity to the light chain sequence as depicted in FIG. 2 also provide desired binding properties, as evidenced by antibody AM22. Further provided is therefore an isolated, synthetic or recombinant antibody or a functional part, derivative and/or analogue thereof according to the invention, having a heavy chain sequence comprising a sequence which has at least 70% sequence identity to the sequence QVQLVQSGAEVKKPGATVKVSCKISGHT-LIKLSIHWVRQAPGKGLEWMGG YEGEVDEIFYAQK-FQHRLTVIADTATDTVYMELGRLTSDDTAVY-FCGTLGV TVTEAGLGIDDYWGQGTLVTVSS (SEQ ID NO: 16) and/or having a light chain sequence which has at least 70% sequence identity to the sequence EIV-LTQSPGTLSLSPGERATLSCRASQIVSRNHLAWY-QQKPGQAPRLLIFGA SSRATGIPVRFSGSGSGTD-FTLTINGLAPEDFAVYYCLSSDSSIFTFGPGTKV DFK (SEQ ID NO: 32).

An isolated, synthetic or recombinant antibody or a functional part, derivative and/or analogue thereof according to the invention preferably comprises a heavy chain sequence and/or a light chain sequence which is at least 75%, more preferably at least 80%, more preferably at least 85%, more preferably at least 90%, most preferably at least 95% identical to a heavy chain sequence and/or a light chain sequence as depicted in FIG. 2. The higher the homology, the more closely said antibody or functional equivalent resembles antibody AM22. An isolated, synthetic or recombinant antibody or a functional part, derivative and/or analogue thereof according to the invention preferably comprises a heavy chain as well as a light chain which resemble the heavy and light chain of AM22. Further provided is therefore an isolated, synthetic or recombinant antibody or a functional part, derivative and/or analogue thereof comprising a heavy chain sequence and a light chain sequence which are at least 70%, more preferably at least 80%, more preferably at least 85%, more preferably at least 90%, most preferably at least 95% identical to the heavy chain sequence and the light chain sequence, respectively, as depicted in FIG. 2. In one embodiment an antibody or functional equivalent is provided which has a heavy chain sequence as depicted in FIG. 2 and a light chain sequence as depicted in FIG. 2.

One embodiment provides an isolated, synthetic or recombinant antibody or a functional part, derivative and/or analogue thereof comprising a heavy chain sequence consisting of the heavy chain sequence as depicted in FIG. 2, and/or comprising a light chain sequence consisting of the light chain sequence as depicted in FIG. 2. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')$_2$ fragment or a single domain antibody or a single chain antibody or a nanobody or an unibody or a scFV fragment based on a heavy chain sequence or light chain sequence depicted in FIG. 2 is produced. A functional part of an antibody comprising at least a functional part of a sequence as depicted in FIG. 2 is therefore also provided. Said functional part has a length of at least 20 amino acids and comprises at least one sequence selected from the group consisting of a sequence which is at least 70% identical to the heavy chain CDR1 sequence depicted in FIG. 2 and a sequence which has at least 70% sequence identity to the heavy chain CDR2 sequence depicted in FIG. 2 and a sequence which has at least 70% sequence identity to the heavy chain CDR3 sequence depicted in FIG. 2 and a sequence which has at least 70% sequence identity to the light chain CDR1 sequence depicted in FIG. 2 and a sequence which has at least 70% sequence identity to the light chain CDR2 sequence depicted in FIG. 2 and a sequence which has at least 70% sequence identity to the light chain CDR3 sequence depicted in FIG. 2.

As said before, antibodies and functional equivalents according to the present invention recognize a unique epitope of an RSV F protein trimer. Hence, antibodies and functional equivalents are provided that specifically recognize this epitope. Antibodies or functional equivalents thereof that specifically recognize said unique epitope are preferably combined with RSV-specific antibodies that are already known, such as palivizumab, D25, AM14, AM16 and AM23. By combining an antibody or functional equivalent according to the invention that specifically recognizes said unique epitope with a known RSV-specific antibody, two or more different epitopes of RSV are recognized during the same therapy. This way, a stronger immunogenic response to RSV and/or a higher antibody specificity against RSV is reached With a stronger immunogenic response to and higher specificity against RSV, such combination will result in more effective treatment and/or prevention of a RSV-related disorder.

Therefore, the invention provides an isolated, synthetic or recombinant antibody or a functional part, derivative and/or analogue thereof which is capable of specifically binding an epitope that is recognized by an antibody which comprises:
a heavy chain CDR1 sequence comprising the sequence KLSIH (SEQ ID NO: 4), and/or
a heavy chain CDR2 sequence comprising the sequence GYEGEVDEIFYAQKFQH (SEQ ID NO: 8), and/or a heavy chain CDR3 sequence comprising the sequence LGVTVTEAGLGIDDY (SEQ ID NO: 12), and/or
a light chain CDR1 sequence comprising the sequence RASQIVSRNHLA (SEQ ID NO: 20), and/or
a light chain CDR2 sequence comprising the sequence GASSRAT (SEQ ID NO: 24), and/or
a light chain CDR3 sequence comprising the sequence LSSDSSI (SEQ ID NO: 28).

In a particularly preferred embodiment the invention provides an isolated, synthetic or recombinant antibody or a functional part, derivative and/or analogue thereof which is capable of specifically binding an epitope that is recognized by an AM22 antibody which comprises:
a heavy chain CDR1 sequence comprising the sequence KLSIH (SEQ ID NO: 4), and
a heavy chain CDR2 sequence comprising the sequence GYEGEVDEIFYAQKFQH (SEQ ID NO: 8), and
a heavy chain CDR3 sequence comprising the sequence LGVTVTEAGLGIDDY (SEQ ID NO: 12), and
a light chain CDR1 sequence comprising the sequence RASQIVSRNHLA (SEQ ID NO: 20), and
a light chain CDR2 sequence comprising the sequence GASSRAT (SEQ ID NO: 24), and
a light chain CDR3 sequence comprising the sequence LSSDSSI (SEQ ID NO: 28).

A further embodiment of the invention contemplates certain antibody constant region (Fc) modifications to alter effector functions. For example, the serum half-life of proteins comprising Fc regions is increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The increase in half-life allows for the reduction in amount of drug given to a patient as well as reducing the frequency of administration. To increase the serum half life of an antibody according to the invention, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, antibodies of the invention with increased half-lives may be generated by modifying amino acid residues identified as involved in the interaction between the Fc and an FcRn receptor (see, for examples, U.S. Pat. Nos. 6,821,505 and 7,083,784). In addition, the half-life of antibodies of the invention may be increased by conjugation to PEG or Albumin by techniques widely utilized in the art. In some embodiments antibodies comprising Fc variant regions of the invention have an increased half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to an antibody comprising a native Fc region. In some embodiments antibodies comprising Fc variant regains have an increased half-life of about 2 fold, about 3 fold, about 4 fold, about 5 fold, about 10 fold, about 20 fold, about 50 fold or more, or is between 2 fold and 10 fold, or between 5 fold and 25 fold, or between 15 fold and 50 fold, as compared to an antibody comprising a native Fc region. The invention therefore provides an antibody, functional part, derivative or analogue according the invention, comprising a salvage receptor binding epitope, and/or modified amino acid residues identified as involved in the interaction between the Fc and an FcRN receptor, and/or non naturally occurring amino acid residues. Another preferred embodiment provides an antibody or functional equivalent according to the invention which is conjugated to PEG or Albumin.

In one embodiment, the present invention provides Fc variants according to the invention, wherein the Fc region comprises a modification (e.g., amino acid substitution, amino acid insertion, amino acid deletion) at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat et al (J Immunol. 1991; 147(5):1709-19). Optionally, the Fc region comprises a non naturally occurring amino acid residue at additional and/or alternative positions known to one skilled in the art (see, e.g., U.S. Pat. Nos. 5,624,821; 6,277,375; 6,737,056; 7,083,784; 7,317,091; 7,217,797; 7,276,585; 7,355,008; 2002/0147311; 2004/0002587; 2005/0215768; 2007/0135620; 2007/0224188; 2008/0089892; WO 94/29351; and WO 99/58572).

In a specific embodiment, the present invention provides an Fc variant antibody according to the invention, wherein the Fc region comprises at least one non-naturally occurring amino acid at one or more positions selected from the group consisting of 252, 254, and 256. In one embodiment, the non-naturally occurring amino acids are selected from the group consisting of 252Y, 254T and 256E.

The present invention provides RSV-specific antibodies and functional equivalents thereof having improved properties as compared to prior art antibodies. The inventors have succeeded in generating RSV-specific antibodies with the lowest $IC_{50}$ value currently known. Such antibodies have a particular high or strong affinity for RSV and are therefore particularly suitable for counteracting and/or at least in part preventing an RSV-infection and/or adverse effects of an RSV infection. One embodiment therefore provides an antibody which has an $IC_{50}$ value of less than 1.25 ng/ml, preferably less than 1.2 ng/ml, more preferably less that 1.19 ng/ml, more preferably less than 1.18 ng/ml, and most preferably between 1.1 ng/ml and 1.17 as determined in the in vitro neutralization assay described in the examples (see FIG. 1).

The invention further provides an isolated, synthetic or recombinant nucleic acid sequence or a functional equivalent thereof with a length of at least 15 nucleotides, preferably at least 30 nucleotides, more preferably at least 50 nucleotides, more preferably at least 75 nucleotides, encoding at least an antigen-binding part of an antibody or functional equivalent according to the invention. Such nucleic acid is for instance isolated from a B-cell which is capable of producing an antibody according to the invention. A preferred embodiment provides a nucleic acid sequence comprising a sequence which has at least 70% sequence identity to at least 15 nucleotides of a nucleic acid sequence as depicted in FIG. 2. A nucleic acid sequence according to the invention preferably comprises a sequence which has at least 75%, more preferably at least 80%, more preferably at least 85%, more preferably at least 90%, most preferably at least 95% sequence identity to at least 15 nucleotides of a nucleic acid sequence as depicted in FIG. 2. Preferably, said nucleic acid sequence as depicted in FIG. 2 comprises at least one CDR encoding sequence.

One preferred embodiment provides an isolated, synthetic or recombinant nucleic acid sequence with a length of at least 15 nucleotides, or a functional equivalent thereof, encoding at least one CDR sequence of an antibody or functional equivalent according to the invention. Said nucleic acid sequence preferably encodes at least one CDR sequence which has at least 70% sequence identity to a CDR region of antibody AM22. Nucleic acid sequences encoding AM22 CDR regions are depicted in FIG. 2. Further provided is therefore an isolated, synthetic or recombinant nucleic acid sequence, or a functional equivalent thereof, comprising a sequence which has at least 70% sequence identity to a sequence selected from the group consisting of aaattatccattcac (SEQ ID NO: 3), ggttatgagggtgaggtcgatgagattttctacgcacagaagttccagcac (SEQ ID NO: 7), ctaggtgtgacagtgactgaggctggactggggatcgatgactac (SEQ ID NO: 11), agggccagtcagattgttagcaggaaccacttagcc (SEQ ID NO: 19), ggtgcgtccagtcgggccact (SEQ ID NO: 23) and ctgtcctctgattcctccata (SEQ ID NO: 27).

Said nucleic acid sequences or functional equivalent preferably comprises a sequence which has at least 75%, more preferably at least 80%, more preferably at least 85%, more preferably at least 90% sequence identity to any of the above mentioned nucleic acid sequences. Further provided is a nucleic acid sequence or functional equivalent thereof comprising a sequence which has at least 70% sequence identity to at least part of a nucleotide sequence as depicted in FIG. 2, said part having at least 15 nucleotides and encoding at least one CDR region as depicted in FIG. 2.

A nucleic acid sequence or functional equivalent thereof according to the present invention preferably encodes a region which has at least 70% sequence identity to an AM22 CDR region, an AM22 heavy chain and/or an AM22 light chain. One embodiment thus provides an isolated, synthetic or recombinant nucleic acid sequence, or a functional equivalent thereof, comprising a sequence encoding an amino acid sequence which has at least 70% sequence identity to the sequence KLSIH (SEQ ID NO: 4), and/or at least 70% sequence identity to the sequence GYEGEVDEIFYAQKFQH (SEQ ID NO: 8), and/or at least 70% sequence identity to the sequence LGVTVTEAGLGIDDY (SEQ ID NO: 12), and/or at least 70% sequence identity to the sequence RASQIVSRNHLA (SEQ ID NO: 20), and/or at least 70% sequence identity to the sequence GASSRAT (SEQ ID NO: 24), and/or at least 70% sequence identity to the sequence LSSDSSI (SEQ ID NO: 28), and/or at least 70% sequence identity to the sequence QVQLVQSGAEVKKPGATVKVSCKISGHTLIKLSIHWVRQAPGKGLEWMGG YEGEVDEIFYAQKFQHRLTVIADTATDTVYMELGRLTSDDTAVYFCGTLGV TVTEAGLGIDDYWGQGTLVTVSS (SEQ ID NO: 16), and/or at least 70% sequence identity to the sequence EIVLTQSPGTLSLSPGERATLSCRASQIVSRNHLAWYQQKPGQAPRLLIFGA SSRATGIPVRFSGSGSGTDFTLTINGLAPEDFAVYYCLSSDSSIFTFGPGTKV DFK (SEQ ID NO: 32).

As said before, an antibody or functional equivalent according to the invention is capable of recognizing a unique epitope present on trimeric RSV F proteins. A nucleic acid sequence according to the invention thus preferably encodes a CDR sequence capable of specifically binding this unique epitope. Also provided by the invention is therefore an isolated, synthetic or recombinant nucleic acid sequence or a functional equivalent thereof, encoding at least one CDR sequence capable of specifically binding an epitope that is recognized by an antibody which comprises:

a heavy chain CDR1 sequence comprising the sequence KLSIH (SEQ ID NO: 4), and/or
a heavy chain CDR2 sequence comprising the sequence GYEGEVDEIFYAQKFQH (SEQ ID NO: 8), and/or
a heavy chain CDR3 sequence comprising the sequence LGVTVTEAGLGIDDY (SEQ ID NO: 12), and/or
a light chain CDR1 sequence comprising the sequence RASQIVSRNHLA (SEQ ID NO: 20), and/or
a light chain CDR2 sequence comprising the sequence GASSRAT (SEQ ID NO: 24), and/or
a light chain CDR3 sequence comprising the sequence LSSDSSI (SEQ ID NO: 28).

Preferably, said nucleic acid sequence encodes a whole antibody or functional equivalent (for instance comprising a heavy chain or light chain) according to the invention. Further provided is therefore an isolated, synthetic or recombinant nucleic acid sequence, or a functional equivalent thereof, encoding an antibody or functional equivalent thereof capable of specifically binding an epitope that is recognized by an antibody which comprises:

a heavy chain CDR1 sequence comprising the sequence KLSIH (SEQ ID NO: 4), and/or
a heavy chain CDR2 sequence comprising the sequence GYEGEVDEIFYAQKFQH (SEQ ID NO: 8), and/or
a heavy chain CDR3 sequence comprising the sequence LGVTVTEAGLGIDDY (SEQ ID NO: 12), and/or
a light chain CDR1 sequence comprising the sequence RASQIVSRNHLA (SEQ ID NO: 20), and/or
a light chain CDR2 sequence comprising the sequence GASSRAT (SEQ ID NO: 24), and/or
a light chain CDR3 sequence comprising the sequence LSSDSSI (SEQ ID NO: 28).

In one embodiment of the invention a nucleic acid sequence or functional equivalent encodes an antibody or a functional part, derivative and/or analogue thereof capable of specifically binding an epitope that is recognized by an AM22 antibody, which comprises a heavy chain CDR1 sequence comprising the sequence KLSIH (SEQ ID NO: 4), and a heavy chain CDR2 sequence comprising the sequence GYEGEVDEIFYAQKFQH (SEQ ID NO: 8), and a heavy chain CDR3 sequence comprising the sequence LGVTVTEAGLGIDDY (SEQ ID NO: 12), and a light chain CDR1 sequence comprising the sequence RASQIVSRNHLA (SEQ ID NO: 20), and a light chain CDR2 sequence comprising the sequence GASSRAT (SEQ ID NO: 24), and a light chain CDR3 sequence comprising the sequence LSSDSSI (SEQ ID NO: 28).

A nucleic acid sequence or functional equivalent according to the invention preferably encodes an antibody or functional equivalent thereof that has a dissociation constant ($K_d$) of less than $1\times10^{-2}$M, $1\times10^{-3}$M, $1\times10^{-4}$M, $1\times10^{-5}$M, $1\times10^{-6}$M, $1\times10^{-7}$M, $1\times10^{-8}$M, $1\times10^{-9}$M, $1\times10^{-10}$M, $1\times10^{-11}$M, $1\times10^{-12}$M, $1\times10^{-13}$M, $1\times10^{-14}$M or less than $1\times10^{-15}$M.

Further provided is a vector comprising a nucleic acid sequence according to the invention. Such vector is suitable for a variety of applications. For instance, a vector of the invention comprising a therapeutically beneficial nucleic acid sequence is suitable for prophylactic or therapeutic applications. Administration of such vector to an individual in need thereof results in expression of said prophylactic or therapeutic nucleic acid sequence in vivo. Said vector can also be used in applications involving in vitro expression of a nucleic acid sequence of interest, for instance for (commercial) production of antibodies or functional equivalents according to the invention. Methods for constructing a vector with a nucleic acid sequence according to the invention are well known in the art. Non-limiting examples of vectors suitable for generating a vector of the invention are retroviral and lentiviral vectors.

The term "% sequence identity" is defined herein as the percentage of residues in a candidate amino acid sequence or candidate nucleic acid sequence that is identical with the residues in a reference sequence after aligning the two sequences and introducing gaps, if necessary, to achieve the maximum percent identity. Methods and computer programs for the alignment are well known in the art.

As used herein, a nucleic acid molecule or nucleic acid sequence of the invention preferably comprises a chain of nucleotides, more preferably DNA and/or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid sequence" also encompasses a chain comprising non-natural nucleotides, modified nucleotides and/or non-nucleotide building blocks which exhibit the same function as natural nucleotides.

A nucleic acid sequence or vector according to the present invention is particularly useful for generating antibodies or functional equivalents which are specific for RSV. This is for instance done by introducing such nucleic acid sequence or vector into a cell so that the cell's nucleic acid translation machinery will produce the encoded antibody or functional equivalent. In one embodiment, a nucleic acid sequence or vector encoding a heavy and/or light chain according to the invention is expressed in so called producer cells, such as for instance cells of a Chinese hamster ovary (CHO), NSO (a mouse myeloma) or 293(T) cell line, some of which are adapted to commercial antibody production. Proliferation of said producer cells results in a producer cell line capable of producing antibodies or functional equivalents thereof according to the present invention. Preferably, said producer cell line is suitable for producing antibodies for use in humans. Hence, said producer cell line is preferably free of pathogenic agents such as pathogenic micro-organisms. Most preferably, antibodies or functional equivalents consisting of human sequences are generated using at least one nucleic acid sequence or vector according to the invention.

An isolated or recombinant antibody producing cell capable of producing an antibody or a functional part, derivative and/or analogue thereof according to the invention is therefore also provided, as well as a method for producing an isolated, synthetic or recombinant antibody or functional part, derivative and/or analogue according to the invention, comprising providing a cell with a nucleic acid sequence or functional equivalent or vector according to the invention and allowing said cell to translate said nucleic acid sequence or functional equivalent or vector, thereby producing said antibody or functional part, derivative and/or analogue thereof.

An antibody producing cell is defined herein as a cell which is capable of producing and/or secreting antibody or a functional equivalent thereof, and/or which is capable of developing into a cell which is capable of producing and/or secreting antibody or a functional equivalent thereof. An antibody producing cell according to the invention is preferably a producer cell which is adapted to commercial antibody production. Preferably, said producer cell is suitable for producing antibodies for use in humans.

A method according to the invention preferably further comprises a step of harvesting, purifying and/or isolating said antibody or functional part, derivative and/or analogue thereof according to the invention. Obtained antibodies or functional equivalents according to the invention are preferably used in human therapy, optionally after additional purifying, isolation or processing steps.

Now that improved Respiratory Syncytial Virus-specific antibodies or functional equivalents according to the invention and nucleic acid sequences and vectors coding therefore have been provided, including human antibodies or functional equivalents, improved prophylactic and/or therapeutic applications have become available. RSV is counteracted by antibodies or functional equivalents according to the invention. An antibody or functional equivalent according to the invention is therefore particularly suitable for use as a medicine or prophylactic agent, optionally in combination with at least one other RSV-specific antibody known in the art. Preferably, antibodies or functional equivalents are used which consist of human sequences, or which have at most 5% of non-human sequences, in order to reduce the chance of adverse side effects when human individuals are treated. An isolated, synthetic or recombinant antibody or a functional part, derivative and/or analogue thereof or a nucleic acid sequence or functional equivalent thereof or a vector or a cell according to the invention for use as a medicament and/or prophylactic agent is therefore also herewith provided. When a nucleic acid or functional equivalent or vector according to the invention is administered, it will be translated in situ into an antibody or functional equivalent according to the invention. In a particularly preferred embodiment said antibody comprises antibody AM22, or a functional equivalent thereof. Said medicament or prophylactic agent is preferably used for counteracting or at least in part preventing an infection by RSV. Further provided is therefore an isolated, synthetic or recombinant antibody or a functional part, derivative and/or analogue thereof or a nucleic acid sequence or functional equivalent thereof or vector or cell according to the invention for use as a medicament and/or prophylactic agent for at least in part treating and/or preventing a disorder related to RSV. A medicament that comprises AM22 in combination with at least one other RSV-specific agent, preferably an antibody, known in the art, is particularly advantageous because with such combination a stronger immunogenic response to RSV is obtained and/or higher antibody specificity against RSV is reached. Further provided is therefore a combination of an isolated, synthetic or recombinant antibody or a functional part, derivative and/or analogue thereof or a nucleic acid sequence or functional equivalent thereof or vector or cell according to the invention and another, different RSV-specific agent, preferably an antibody or functional equivalent thereof, for use as a medicament and/or prophylactic agent. A combination according to the invention preferably comprises AM22 and an antibody selected from the group consisting of palivizumab, D25, AM14, AM16 and AM23. As said before, such combination is particularly suitable for at least in part treating or preventing a RSV-related disorder. Further provided is therefore a use of a combination according to the invention for the preparation of a medicament and/or prophylactic agent for at least in part treating and/or preventing a disorder related to RSV. A use of an isolated, synthetic or recombinant antibody or a functional part, derivative and/or analogue thereof or a nucleic acid sequence or functional equivalent thereof or vector or cell according to the invention for the preparation of a medicament and/or prophylactic agent for at least in part treating and/or preventing an RSV-related disorder is therefore also provided, as well as a method for at least in part treating or preventing a RSV-related disorder, the method comprising administering to an individual in need thereof a therapeutically effective amount of an isolated, synthetic or recombinant antibody or a functional part, derivative and/or analogue thereof according to the invention. In one preferred embodiment, a combination with at least one other RSV-specific agent, preferable another RSV specific antibody, is used. Said individual has preferably been diagnosed to be infected by RSV before treatment.

Said antibody preferably comprises antibody AM22, or a functional part thereof. Said at least one other RSV-specific antibody is preferably palivizumab, D25, AM14, AM16 or AM23. Most preferably a combination of AM22 and D25 is used.

In order to at least in part treat or prevent a disorder related to Respiratory Syncytial Virus, an antibody or functional equivalent according to the invention is preferably administered to an individual before an infection has taken place. Alternatively, an antibody or functional equivalent according to the invention is administered when an individual is already infected. Said antibody or functional equivalent is preferably administered to individuals with an increased risk of complications, such as for instance hospitalized individuals and/or individuals with compromised immunity. Also elderly people have an increased risk of RSV infection. Antibodies or functional equivalents according to the invention are preferably administered via one or more injections. Dose ranges of antibodies or functional equivalents according to the invention to be used in the prophylactic or therapeutic applications as described herein before are designed on the basis of rising dose studies in the clinic in clinical trials for which rigorous protocol requirements exist. Typical doses are between 0.1 and 10 mg per kg body weight. For prophylactic or therapeutic application antibodies or functional equivalents according to the invention are typically combined with a pharmaceutically acceptable carrier, diluent and/or excipient. Examples of suitable carriers for instance comprise keyhole limpet haemocyanin (KLH), serum albumin (e.g. BSA or RSA) and ovalbumin. In one preferred embodiment said suitable carrier comprises a solution like for example saline.

In yet another embodiment a nucleic acid or a vector encoding an antibody or functional equivalent according to the invention is used. As already described, upon administration of such nucleic acid or vector, antibodies or functional equivalents are produced by the host's machinery. Produced antibodies or functional equivalents are capable of at least in part preventing and/or counteracting Respiratory Syncytial Virus infection and/or the adverse effects of such infection. A nucleic acid sequence or functional equivalent or a vector according to the invention for use as a medicament and/or prophylactic agent is therefore also herewith provided. Further provided is a use of a nucleic acid sequence or functional equivalent or vector according to the invention for the preparation of a medicament and/or prophylactic agent for at least in part treating and/or preventing a RSV-related disorder.

Further provided is a pharmaceutical composition comprising an isolated, synthetic or recombinant antibody or a functional part, derivative and/or analogue thereof or a nucleic acid sequence or functional equivalent thereof or vector or cell according to the invention and a pharmaceutical acceptable carrier, diluent or excipient. Said pharmaceutical composition is preferably suitable for human use. In one preferred embodiment said antibody is AM22. In a further preferred embodiment said nucleic acid encodes AM22 or a functional equivalent thereof. In one embodiment said pharmaceutical composition further comprises at least one other RSV-specific antibody, preferably palivizumab, D25, AM14, AM16 and/or AM23.

The invention is further explained in the following examples. These examples do not limit the scope of the invention, but merely serve to clarify the invention.

REFERENCES

Chen Y, Wiesmann C, Fuh G, Li B, Christinger H W, McKay P, de Vos A M, Lowman H B. Selection and analysis of an optimized anti-VEGF antibody: crystal structure of an affinity-matured Fab in complex with antigen. J Mol Biol. 1999; 293(4):865-81.

Diehl S A, Schmidlin H, Nagasawa M, van Haren S D, Kwakkenbos M J, Yasuda E, Beaumont T, Scheeren F A, Spits H. STAT3-mediated up-regulation of BLIMP1 Is coordinated with BCL6 down-regulation to control human plasma cell differentiation. J Immunol. 2008; 180(7):4805-15.

Jaleco A C, Stegmann A P, Heemskerk M H, Couwenberg F, Bakker A Q, Weijer K, Spits H. Genetic modification of human B-cell development: B-cell development is inhibited by the dominant negative helix loop helix factor Id3. Blood. 1999; 94(8):2637-46.

Kabat E A, Wu T T. Identical V region amino acid sequences and segments of sequences in antibodies of different specificities. Relative contributions of VH and VL genes, minigenes, and complementarity determining regions to binding of antibody-combining sites. J Immunol. 1991; 147(5):1709-19.

Kwakkenbos M J, Diehl S A, Yasuda E, Bakker A Q, Van Geelen C M M, Lukens M V, Van Bleek G M, Widjojoatmodjo M N, Bogers W M J M, Mei H, Radbruch A, Scheeren F A, Spits H and Beaumont T. Generation of stable monoclonal antibody-producing BCR+ human memory B cells by genetic programming. Nat Med. 2009 In press.

Shvarts A, Brummelkamp T R, Scheeren F, Koh E, Daley G Q, Spits H, Bernards R. A senescence rescue screen identifies BCL6 as an inhibitor of anti-proliferative p19 (ARF)-p53 signaling. Genes Dev. 2002; 16(6):681-6, Scheeren F A, Naspetti M, Diehl S, Schotte R, Nagasawa M, Wijnands E, Gimeno R, Vyth-Dreese F A, Blom B, Spits H. STAT5 regulates the self-renewal capacity and differentiation of human memory B cells and controls Bcl-6 expression. Nat Immunol. 2005; 6(3):303-13.

Ternette N, Tippler B, Uberla K, Grunwald T. Immunogenicity and efficacy of codon optimized DNA vaccines encoding the F-protein of respiratory syncytial virus. Vaccine. 2007; 25(41):7271-9.

U.S. Pat. No. 5,624,821
U.S. Pat. No. 5,739,277
U.S. Pat. No. 6,277,375
U.S. Pat. No. 6,737,056
U.S. Pat. No. 6,821,505
U.S. Pat. No. 7,083,784
U.S. Pat. No. 7,317,091

U.S. Pat. No. 7,217,797
U.S. Pat. No. 7,276,585
U.S. Pat. No. 7,355,008
US 2002/0147311
US 2004/0002587
US 2005/0215768
US 2007/0135620
US 2007/0224188
US 2008/0089892
WO 94/29351
WO 99/58572
WO 2008/147196

BRIEF DESCRIPTION OF THE DRAWINGS

FIGS. 2A and 2B. FIG. 2A shows AM22 heavy chain nucleotide sequences and amino acid sequences. FIG. 2B shows light chain nucleotide sequences and amino acid sequences.

FIG. 3A shows binding of the antibodies to EL-4 cells infected with Vesicular Stomatitis Virus (VSV) which was pseudotyped with the RSV F or RSV G protein. FIG. 3B shows binding of the anti-RSV F antibodies to ELISA plates that were coated with a lysate of RSV infected HEp2 (left panel) or with Ni-NTA HisSorp Plates (Qiagen) coated with recombinant HIS tagged F protein (right panel). Antibody binding to the F protein is detected with HRP-conjugated IgG detection antibody (dilutions 1:2500, Jackson). FIG. 3C shows binding of the recombinant RSV F Long strain containing a poly HIS tag to the original B cell clones, binding to the BCR is detected with an anti-pentaHIS antibody. FIG. 3D shows the intracellular binding of the human anti-RSV antibodies to 293T cells transfected with a recombinant RSV F construct containing a trimerization domain (ILZ domain).

FIG. 4A shows the retrieval of human IgG1 from serum at day 1 and day 5 after intramuscular administration of indicated doses of antibodies in Cotton rats. FIG. 4B shows the RSV load in the lungs of Cotton rats treated with the indicated antibodies 24 hours before infection with RSV-X. RSV load was determined 5 days after infection with $TCID_{50}$ culture. Experiments were performed twice with four to six individual animals per treatment group. Lung pathology was studied in the same animal groups (FIG. 4C), indicated is the average lung pathology of AM22 and palivizumab, see also table 2.

EXAMPLES

Example 1. B Cell Culture, Immortalization and Selection

Methods

Figure 1:
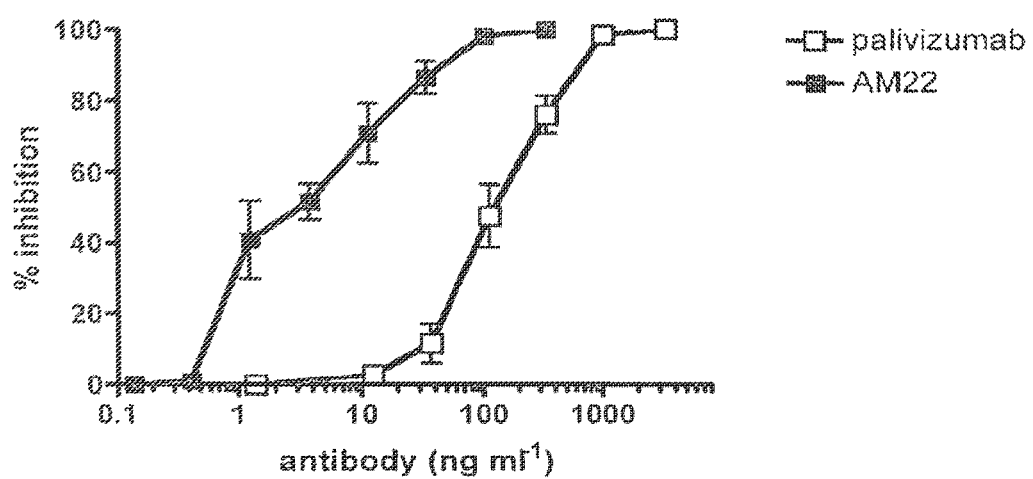
FIG. 1. AM22, a novel fully human monoclonal antibody, neutralizes the RSV A2 virus very efficiently on Hep2 cells compared to palivizumab.

B cells were immortalized and cultured as described before (Scheeren F A, et al. (2005) Nat Immunol 6:303-813; Diehl S A, et al. (2008) J Immunol 180:4805-4815 and Kwakkenbos M J, et al. (2009) Nat Med in press. In brief, we isolated B cells from peripheral blood (Sanquin, Amsterdam, The Netherlands) by Ficoll separation, CD22 MACS microbeads (Miltenyi Biotech) and subsequently cell sorting for CD19+CD3-CD27+IgM-IgA-(IgG memory cells) on a FACSAria (Becton Dickinson). The use of these tissues was approved by the medical ethical committees of the institution and was contingent on informed consent. Retroviral transduced B cells, were maintained at $2 \times 10^5$ cells ml$^{-1}$ in IMDM supplemented with recombinant mouse IL-21 (25 ng ml$^{-1}$, R&D systems) and co-cultured with γ-irradiated (50 Gy) mouse L cell fibroblasts stably expressing CD40L (CD40L-L cells, $10^5$ cells ml$^{-1}$) for 36 hours. The BCL6 and Bcl-xL retroviral constructs were described previously (Shvarts A, et al. (2002) Genes Dev 16:681-686 and Jaleco A C, et al. (1999) Blood 94: 2637-2646)) and were cloned into the LZRS retroviral vector and transfected in Phoenix packaging cells as described before and added to the stimulated B cells (Shvarts A, et al. (2002) Genes Dev 16:681-686 and Scheeren F A et al. (2005) Nat Immunol 6:303-313). Transduced B cells were maintained in IMDM, in the presence of recombinant IL-21 and CD40L-L cells for prolonged periods of time. Given the relatively high amounts of secreted antibodies by BCL6+Bcl-xL-transduced B cells we examined whether we could select antigen-specific B cells on the basis of secretion of specific antibody. BCL6+Bcl-xL transduced memory B cells of a healthy donor were seeded at 100 cells/well and expanded with CD40L-L cells and IL-21. After 2 weeks of culture, supernatants were harvested and screened for the presence of RSV-neutralizing antibodies in a microneutralization experiment. Of 384 cultures (100 cells/well), 31 prevented RSV A2 infection of HEp2 cells. Besides the four microcultures from which D25, AM14, AM16, and AM23 were subcloned by limiting dilution, we next obtained AM22. AM22 has a median half maximum inhibitory concentrations ($IC_{50}$) against the RSV-A2 virus of 1.15 ng ml$^{-1}$ (FIG. 1).

To obtain the sequence of the heavy and light chain of the immunoglobulin locus of AM22, we isolated total RNA with the RNeasy® mini kit (Qiagen), generated cDNA, performed PCR and cloned the heavy and light chain variable regions into the pCR2.1 TA cloning vector (Invitrogen). To rule out reverse transcriptase or DNA polymerase induced mutations, we performed several independent cloning experiments. To produce recombinant AM22 mAb we cloned AM22 heavy and light variable regions in frame with human IgG1 and Kappa constant regions into a pcDNA3.1 (Invitrogen) based vector and transiently transfected 293T cells. We purified recombinant AM22 from the culture supernatant with Protein A.

Results

Previously we developed four potent conformational dependent anti-RSV antibodies, named AM14, AM16, AM23 and D25. These antibodies have been described in WO 2008/147196 and by Kwakkenbos M J et al. (2009) Nat Med in press. From the same donor we also discovered AM22, which recognized the RSV virus even more efficiently compared to the other antibodies as is evident from an $IC_{50}$ of 1.15 ng ml$^{-1}$ against the RSV A2 virus (table 1 and FIG. 1). The amino acid sequence of the VH and VL chain of AM22 revealed that this antibody is different from the other antibodies (FIG. 2).

Example 2. In Vitro Binding Experiments

To further determine the antigen specificity of the AM22 antibody we performed in vitro binding experiments to reveal whether the protein recognized the RSV F or G protein and in what type of conformation.

Methods (1) FACS Staining of RSV G or F Protein

Figure 3A:
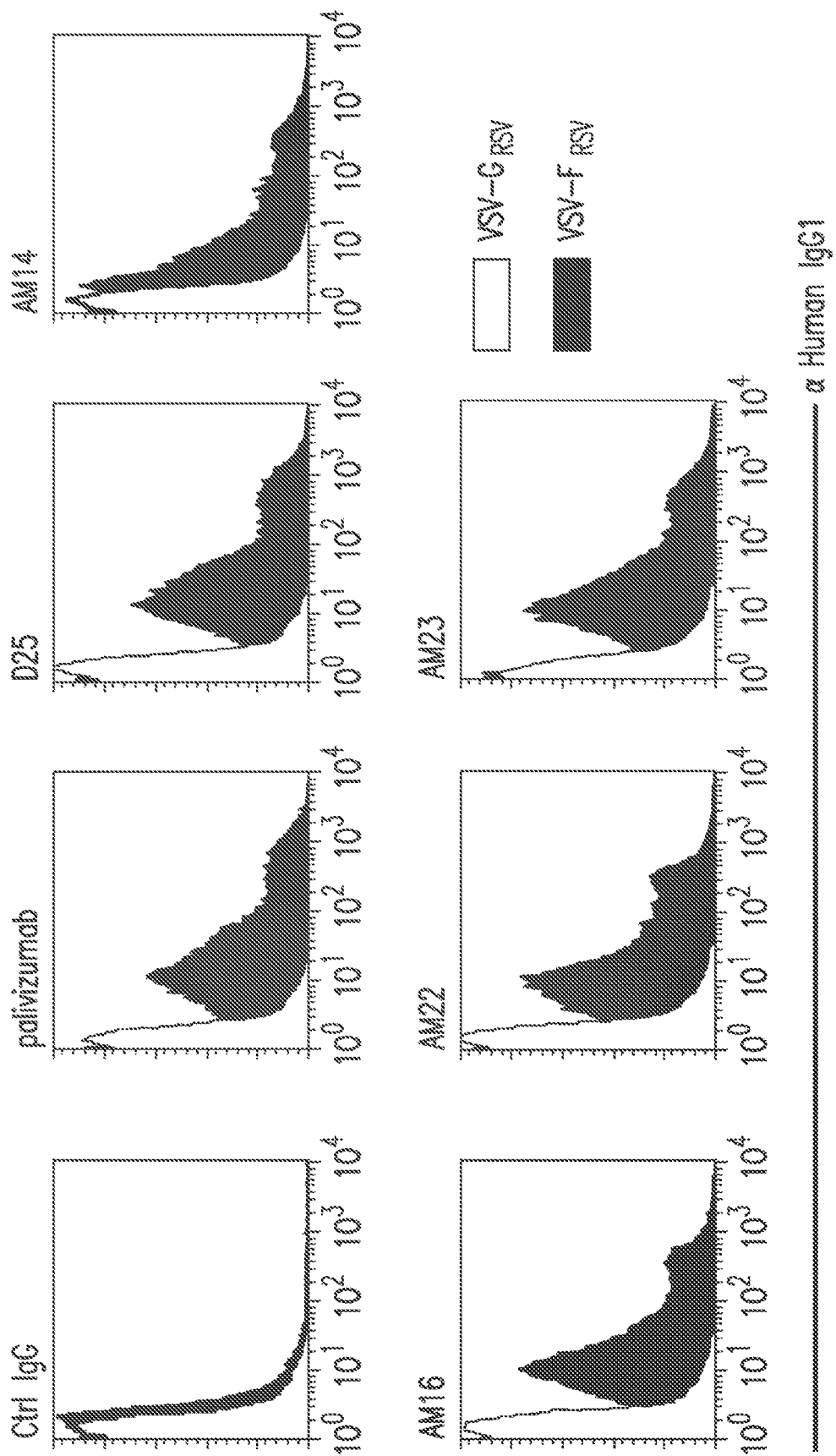
FIGS. 3A-3D. Human anti-RSV monoclonal antibodies recognize conformational epitopes on the Fusion (F) protein of RSV as determined by ELISA and FACS staining.

Virus stock of wild type and recombinant Vesicular Stomatitis Virus (VSV) expressing RSV-G protein (VSV-G) or RSV-F protein (VSV-F) (experiments were performed by M. Lukens at WKZ, Utrecht and VSV viruses were kindly provided by J. S. Kahn and J. K Rose, Yale University School of Medicine) were prepared on BHK cells grown in DMEM containing 5% FCS, penicillin/streptomycin and 50 µM 2-mercapto-ethanol. VSV infection was performed on EL-4 cells that were cultured in Iscove's Modified Dulbecco's medium (IMDM, Gibco, Invitrogen) supplemented with 5% FCS, penicillin/streptomycin and 50 µM 2-mercapto-ethanol. EL-4 cells infected with the VSV virus variants were incubated with recombinant antibody and subsequently stained with mouse-anti-human PE (FIG. 3A).

(2) RSV ELISA

Figure 3B:
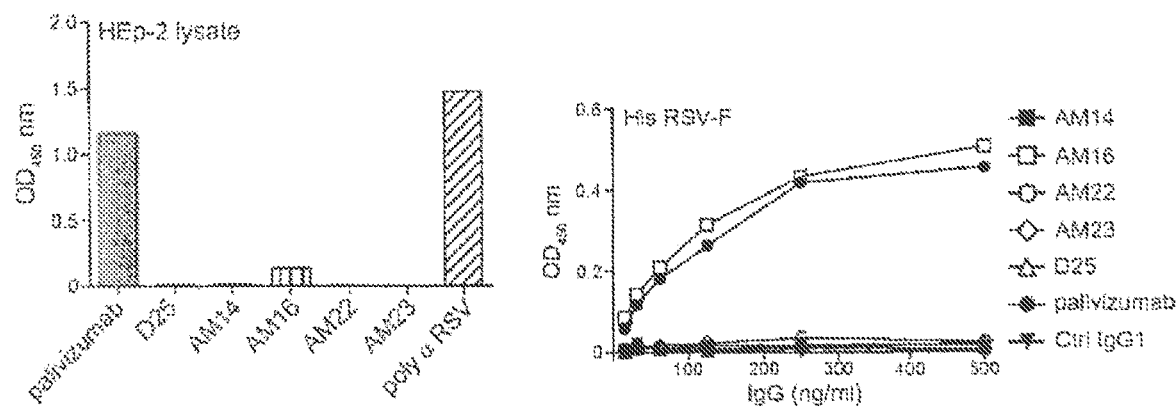
Figure 3C:
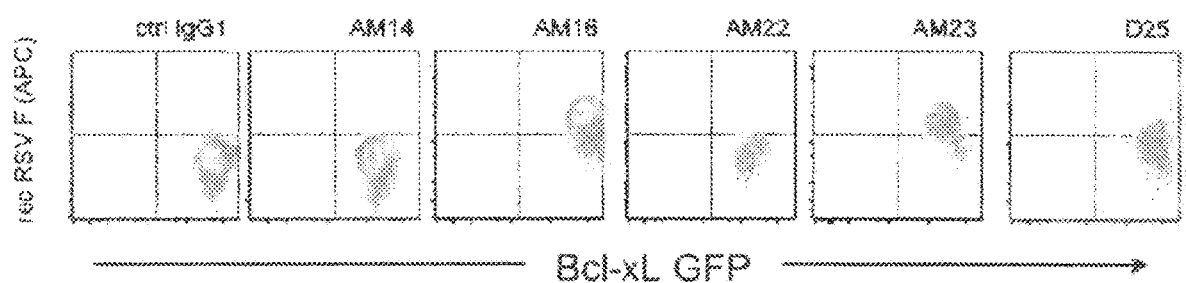

Plates were coated with lysate of RSV infected HEp-2 cells in PBS for 1 hour at 37° C. or o/n at 4° C. and washed in ELISA wash buffer (PBS, 0.5% Tween-20). Plates were blocked by incubation with 4% milk in PBS, before the anti-RSV antibodies or polyclonal goat anti-RSV (Biodesign) in combination with enzyme-conjugated anti-IgG antibodies were added (dilutions 1:2500 for HRP-conjugated anti-IgG (Jackson). TMB substrate/stop solution (Biosource) was used for development of the ELISAs (FIG. 3B left panel). In addition to the lysate of RSV-A2 infected HEp-2 cells, HIS-tagged F protein from RSV Long strain (kindly provided by Frank Coenjaerts, UMCU, Utrecht based on Ternette N, et al. (2007) Vaccine 25:7271-7279) was used to coat Ni-NTA HisSorp Plates (Qiagen) (FIG. 3B right panel). The binding of the RSV F antibodies was detected with HRP-conjugated IgG detection antibody (dilutions 1:2500, Jackson). In another setting the original B cell clones were used for FACS analysis (FIG. 3C). The B cells were incubated with the recombinant HIS tagged F protein and binding to the BCR was detected with a labeled anti-penta HIS antibody ALEXA fluor 647 (Qiagen).

(3) RSV Trimers

Figure 3D:
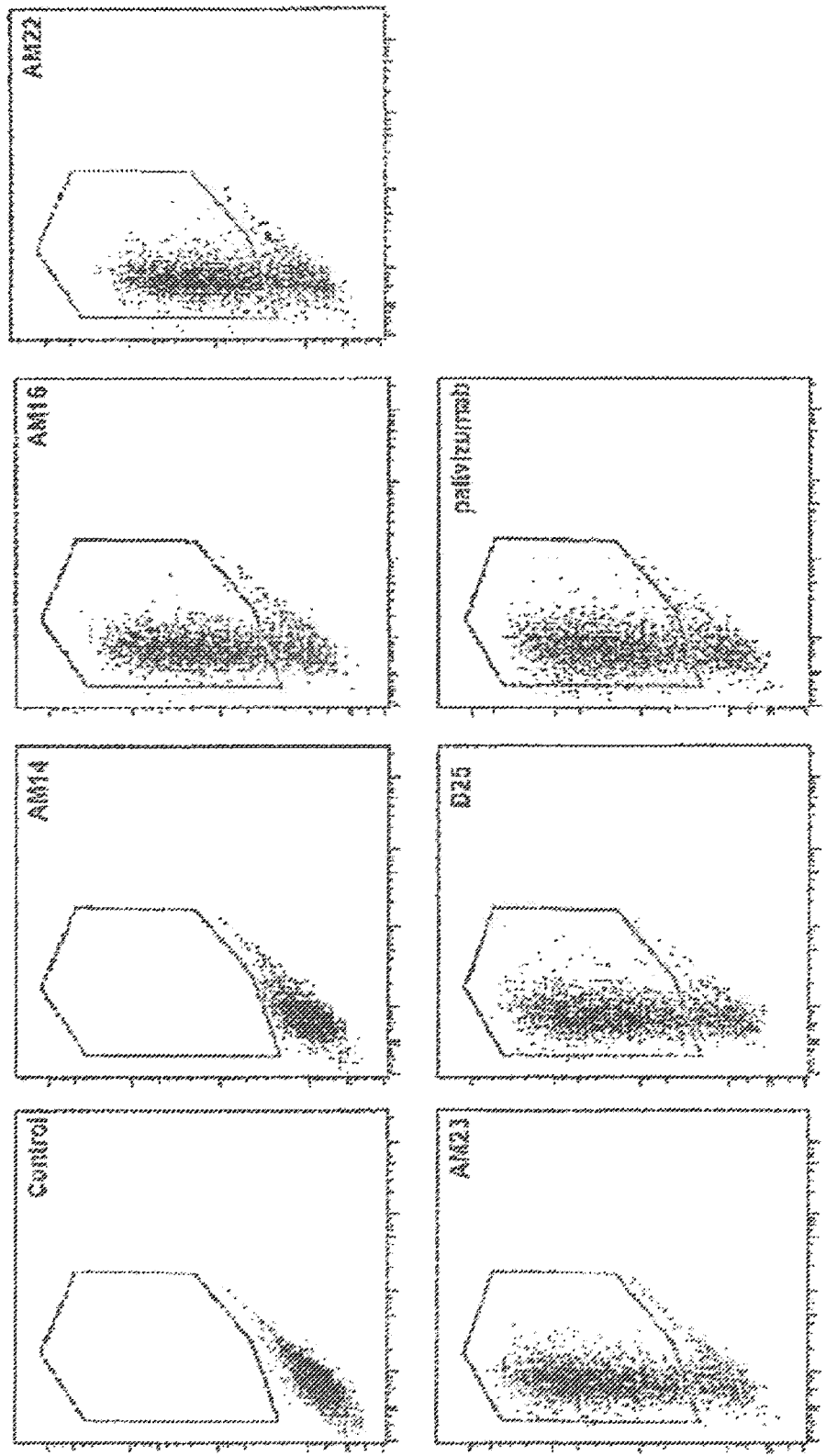

In addition to the recombinant RSV long strain derived F protein we created RSV A2 F trimers by inserting the open reading frame of F into a construct which is fused to an isoleucine zipper domain followed by 8 HIS repeats (ILZ-8×HIS). Protein constructs were transiently expressed in 293T cells and detected by using an intracellular staining protocol using the Fix Perm kit of BD (FIG. 3D).

Results

All antibodies recognized the RSV-F protein when expressed by recombinant VSV (FIG. 3A). Furthermore, except for AM16, recognition was dependent on the presence of conformational epitopes in the RSV-F protein since they did not recognize a lysate of RSV infected HEp-2 cells (FIG. 3B left panel). Also purified HIS-tagged recombinant RSV-F Long strain protein was not recognized by D25, AM14, AM22 and AM23 when tested in a direct ELISA (FIG. 3B right panel). However when the original stable BCR expressing B cell lines were incubated with this non-purified culture supernatant of the HIS tagged RSV-F protein we did observe binding to the B cell clones AM16, AM23 and less strong to D25 (FIG. 3C). The protein in this non-purified culture supernatant possibly contains a fraction of RSV F trimers that do bind the BCR but are only captured as monomers on the HisSorp Plates. However still no RSV-F protein capture was observed to the BCRs of the AM14 and the AM22 B cell lines (FIG. 3C). Thus AM14 and AM22 bind to different epitopes. Possibly, a low percentage of protein F homotrimers or dimers was present in the untreated culture supernatant of the F protein producing cell line. These more native F conformations may express the epitopes recognized by AM23 and D25, which were lost in the denaturing conditions of the ELISA procedures. Interestingly when we performed an intracellular staining on 293T cells transfected with the RSV trimerization construct containing the ILZ-8×HIS sequence we found that AM22 did recognize RSV F (FIG. 3D), however AM14 still did not recognize this protein structure. Thus AM22 is unique since it recognizes a conformation of the RSV-F protein that is not present in denaturing conditions and thus is not present in the monomeric form of the protein. Only when the RSV F proteins are forced to stay together and form trimers then we can detect F binding by the AM22 antibody, a conformation that is present on virus particles and thus explain the high neutralizing potency of AM22.

Example 3. In Vivo Potency Experiments

To study the in vivo potency of the AM22 monoclonal antibody we performed Cotton rat experiments.

Methods

Pathogen free 7-9 week-old Cotton rats (*Sigmodon hispidus*, Harlan Laboratories, Nederland) were anesthetized with isoflurane and given 0.1 ml of purified antibody by intramuscular (i.m.) injection at doses of 2.0 or 0.4 mg kg$^{-1}$ for the control antibody, palivizumab, AM22, AM23 and D25, while AM14 was administered at 0.4 and 0.1 mg kg$^{-1}$. Twenty-four hours later, animals were anesthetized, bled for serum hIgG determination and challenged by intranasal instillation of $10^6$ TCID$_{50}$ RSV-X (100 µl). Five days later animals were sacrificed and their lungs were harvested. Lung virus titers were determined and the lowest limit of detection was 2.1 log$_{10}$ TCID$_{50}$ g$^{-1}$. The Animal Experiment Committee of the Netherlands Vaccine Institute approved all procedures involving Cotton rats.

Results

Figure 4A:
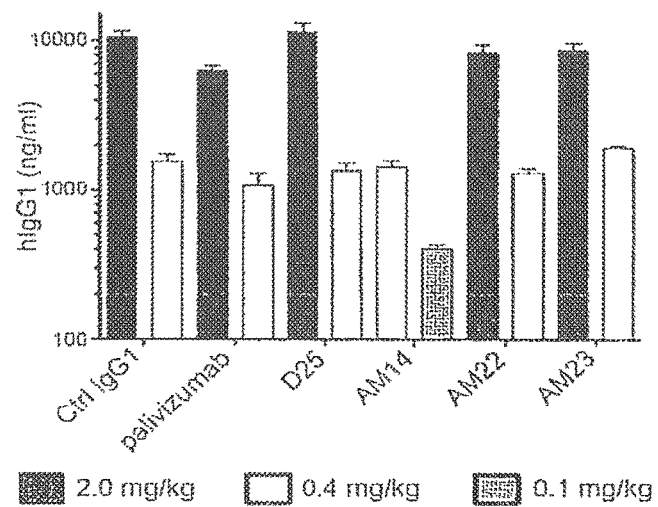
FIGS. 4A-4C. RSV challenge in Cotton rats prophylactically treated with human immunoglobulins.

The anti-RSV antibody panel, except AM16, was tested in Cotton rats. Animals were prophylactically treated with 2.0 or 0.4 mg kg$^{-1}$ of monoclonal antibodies before RSV-X, a primary RSV A isolate, was intra-nasally administered. Due to relatively low antibody production, the AM14 antibody was administered at 0.4 and 0.1 mg kg$^{-1}$. The level of recovered human IgG from Cotton rat sera at day 1 (day of virus inoculation) and day 5 (day of sacrifice) was in the same range for all antibodies and the decline of antibodies in time was comparable (FIG. 4A).

Figure 4B:
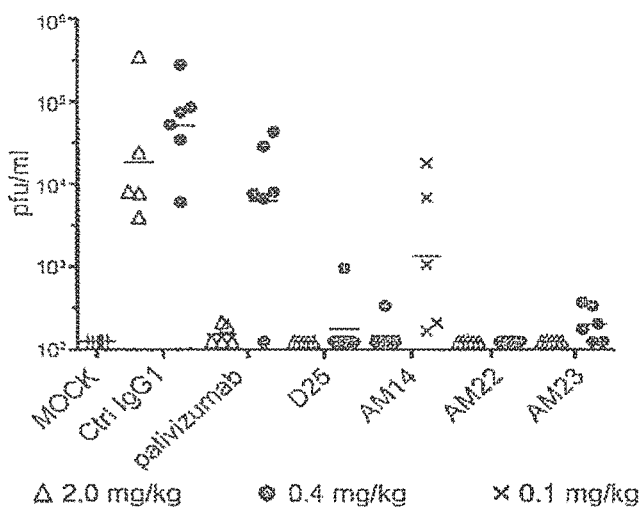

The retrieval of RSV virus from the lungs of sacrificed animals was strongly reduced in all animal groups treated with 2.0 mg/kg of immunoglobulin compared to the control group (FIG. 4B). Animals treated with 0.4 mg kg$^{-1}$ palivizumab and AM23 showed significant virus replication, while in the AM14 and D25 groups one out of 6 animals showed detectable virus replication. No virus could be retrieved from animals treated with AM22. Those results demonstrate that AM22, that specifically recognized conformational epitopes on the RSV F protein, harbors strong in vivo neutralizing capacities.

Analysis of Lung Pathology of RSV Challenged Cotton Rats

Figure 4C:
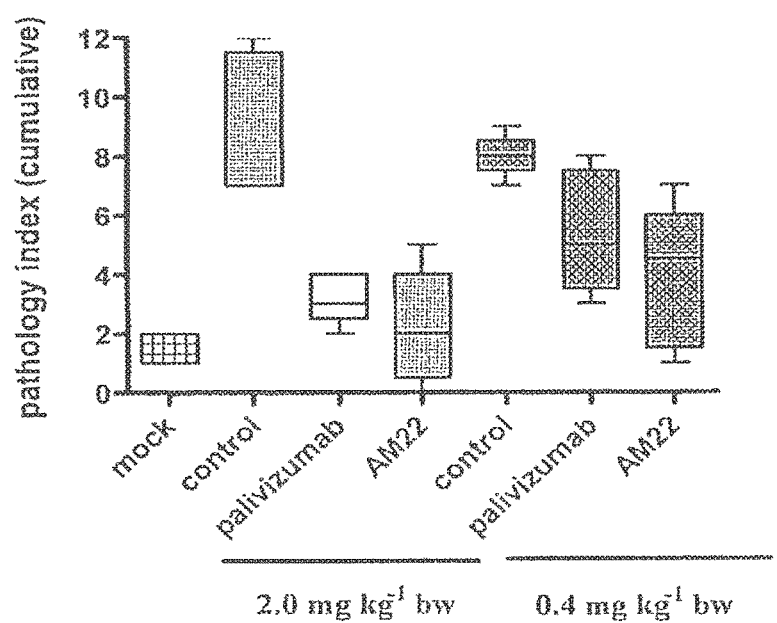

From each Cotton rat at day 5 after i.n. RSV infection the left lung was removed and fixed with formalin. Lung damage was classified between 0-5 for three individual markers: 1) hypertrophy of bronchus and bronchioli epithelia, 2) inflammation surrounding bronchus and bronchioli (peribronchiolitis) and 3) inflammation in the alveoli (alveolitis). The average sum of the scores of all animals in one group created the pathology index (maximum score 15) (FIG. 4c, table 2). Lung pathology after RSV infection was significantly reduced in animal groups treated with high doses of immunoglobulin (2 mg kg$^{-1}$) (table 3). However only in the AM14, AM22 and AM23 groups the pathology was significantly reduced at lower concentrations (0.4 mg kg$^{-1}$). While a complete absence of pathology was seen in 3 out of 5 animals treated with AM22 and AM23 at 2 mg kg$^{-1}$, at 0.4 mg kg$^{-1}$ complete protection was detected in 2 or 1 out of 6 animals in the AM14 and AM22 groups respectively (table 3).

When combining the results of examples 1, 2 and 3 it is concluded that AM22 has certain advantages. AM22 demonstrates the lowest IC$_{50}$ value, meaning that with a lower amount of AM22 similar prophylactic or therapeutic effects are achieved as compared with other antibodies. AM22 recognizes a different epitope of the RSV F protein than the other antibodies and therefore can be used in combination with one of the other antibodies to achieve a stronger immunogenic response to RSV and higher antibody specificity against RSV. Finally, treatment of Cotton rats with AM22 resulted in nearly complete inhibition of virus replication with potential complete absence of pathology in these Cotton rats.

Example 4: Affinity of AM22 for the RSV F Protein

Determining the affinity constant and specificity of binding between the RSV F protein and AM22 is preferred to establish the prophylactic, therapeutic and diagnostic value of the antibody. This is a challenging feature since the antibody affinity has to be determined for an oligomeric protein structure. Usually affinity constants are determined against immobilized agents that are captured on a chip. However protein F captured on a chip would not be recognized by the AM14, AM22, AM23 and D25 antibodies.

Method

"Binding affinity" generally refers to the strength of the sum total of the noncovalent interactions between a single binding site of a molecule (e.g., an antibody) and its binding partner (e.g., an antigen). The affinity of a molecule X for its partner Y can generally be represented by the equilibrium dissociation constant (Kd), which is calculated as the ratio $k_{off}/k_{on}$. Affinity can be measured by common methods known in the art, such as a surface plasmon resonance (SPR) assay. Affinities (KD), on-rates (ka) and off-rates (kd) will be measured by SPR analysis with the IBIS-iSPR instrument at IBIS Technologies BV (Hengelo, the Netherlands). Briefly, anti-RSV antibodies are immobilized and purified RSV F protein (containing penta-HIS) is diluted and rate and affinity constants are measured by injection of at least three serial dilutions of the protein.

Another set up in the IMIS-iSPR machine is to immobilize 1) an anti-penta HIS antibody on which the F-penta HIS protein is coupled or 2) F-penta HIS protein is directly immobilized on the chip and then samples on the chip are incubated with the AIMM antibodies to determine the affinity constants.

TABLE 1

RSV neutralizing activity of purified IgGs.

| | RSV A2$^a$ |
|---|---|
| palivizumab | 152 |
| D25 | 1.28 |

TABLE 1-continued

RSV neutralizing activity of purified IgGs.

| | RSV A2$^a$ |
|---|---|
| AM14 | 2.09 |
| AM16 | 78.7 |
| AM22 | 1.15 |
| AM23 | 4.18 |

The IC$_{50}$ (ng/ml) values of the selected anti-RSV IgGs were determined with standard TCID$_{50}$ culture assay on HEp2 cells, with the RSV A2 virus.

TABLE 2

Cumulative pathology score in Cotton rats.

| antibody | mg/kg | Pathology score (SEM) | P values |
|---|---|---|---|
| Palivizumab | 2.0 | 3.20 (0.4) | 0.0005 |
| Palivizumab | 0.4 | 5.40 (0.8) | <0.05 |
| D25 | 2.0 | 3.40 (0.4) | 0.0005 |
| D25 | 0.4 | 5.83 (1.0) | 0.05 |
| AM14 | 0.4 | 4.20 (0.8) | 0.05 |
| AM14 | 0.1 | 3.67 (1.2) | 0.05 |
| AM22 | 2.0 | 2.75 (0.8) | 0.0005 |
| AM22 | 0.4 | 4.00 (0.9) | <0.05 |
| AM23 | 2.0 | 2.40 (0.2) | 0.0005 |
| AM23 | 0.4 | 3.50 (0.9) | <0.05 |
| Ctrl IgG1 | 2.0 | 8.80 (1.1) | N.A. |
| MOCK | N.A. | 1.80 (0.4) | 0.0005 |

Cumulative pathology score of the lungs of Cotton rats, treated 24 hour before RSV infection with the indicated antibodies. Lung specimens obtained 5 days after infection were evaluated by a pathologist randomly. Lung pathology was classified with scores between 0-5 for three individual markers: 1) hyperthropy of bronchus and bronchioli epithelia, 2) peribronchiolitis and 3) alveolitis. Average pathology score (maximum score 15) with standard error of the mean (SEM) and statistical differences in relation to Ctrl IgG1 group was calculated with the 2-sided Wilcoxon test. Experiments were performed twice with four to six individual animals per treatment group. N.A. not applicable.

TABLE 3

Prevention of pathology in Cotton rats.

| antibody | mg/kg | Significant reduction in pathology | No pathology |
|---|---|---|---|
| Palivizumab | 2 | 5/5 | 1/5 |
| Palivizumab | 0.4 | 3/5 | 0/6 |
| D25 | 2 | 5/5 | 0/5 |
| D25 | 0.4 | 2/6 | 0/6 |
| AM14 | 0.4 | 5/6 | 2/6 |
| AM14 | 0.1 | 4/5 | 0/5 |
| AM22 | 2 | 5/5 | 3/5 |
| AM22 | 0.4 | 5/6 | 1/6 |
| AM23 | 2 | 5/5 | 3/5 |
| AM23 | 0.4 | 5/6 | 0/6 |

Number of animals with significant reduction in/or absence of lung pathology at day 5 during RSV-X infection. Experiments were performed twice with four to six individual animals per treatment group.

The invention claimed is:

1. An antibody, or functional part thereof,
wherein the antibody or functional part thereof specifically binds to a Respiratory Syncytial Virus (RSV) F protein, comprises a heavy chain CDR1 sequence comprising the sequence KLSIH (SEQ ID NO:4), a heavy chain CDR2 sequence comprising the sequence GYEGEVDEIFYAQKFQH (SEQ ID NO:8), a heavy chain CDR3 sequence comprising the sequence LGVTVTEAGLGIDDY (SEQ ID NO:12), a light chain CDR1 sequence comprising the sequence RASQIVSRNHLA (SEQ ID NO:20), a light chain CDR2 sequence comprising the sequence GASSRAT (SEQ ID NO:24), and a light chain CDR3 sequence comprising the sequence LSSDSSI (SEQ ID NO:28), and
wherein the antibody, or functional part thereof, comprises a Fc region comprising a modification at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index of Kabat, said modification comprising an amino acid substitution, and/or an amino acid insertion, and/or an amino acid deletion.

2. The antibody or functional part thereof of claim 1, wherein the antibody or functional part thereof comprises a human IgG1 heavy chain.

3. The antibody or functional part thereof of claim 2, wherein the Fc region modification comprises amino acid substitutions at amino acid positions 252, 254, and/or 256.

4. The antibody or functional part thereof of claim 3, wherein the amino acid substitution at amino acid position 252 is a substitution with tyrosine, the amino acid substitution at amino acid position 254 is a substitution with threonine, and/or the amino acid substitution at amino acid position 256 is a substitution with glutamic acid.

5. The antibody or functional part thereof of claim 3, wherein the amino acid substitution at amino acid position 252 is a substitution with tyrosine, the amino acid substitution at amino acid position 254 is a substitution with threonine, and the amino acid substitution at amino acid position 256 is a substitution with glutamic acid.

6. A pharmaceutical composition comprising the antibody or functional part thereof of claim 1.

7. A pharmaceutical composition comprising the antibody or functional part thereof of claim 3.

8. A pharmaceutical composition comprising the antibody or functional part thereof of claim 5.

9. A method for treating and/or preventing a RSV-related disorder, the method comprising administering to an individual in need thereof a therapeutically effective amount of the antibody or functional part thereof of claim 3.

10. A method for treating and/or preventing a RSV-related disorder, the method comprising administering to an individual in need thereof a therapeutically effective amount of the antibody or functional part thereof of claim 5.

11. A pharmaceutical composition comprising an isolated antibody or functional part thereof of claim 1 and at least one other isolated RSV-specific antibody or functional part thereof.

12. The pharmaceutical composition of claim 11 wherein the at least one other isolated RSV-specific antibody or functional part thereof specifically binds to the RSV F protein and comprises:
  a heavy chain comprising the CDR1, CDR2, and CDR3 sequences of palivizumab and a light chain comprising the CDR1, CDR2, and CDR3 sequences of palivizumab; or
  a heavy chain comprising the CDR1, CDR2, and CDR3 sequences of D25 and a light chain comprising the CDR1, CDR2, and CDR3 sequences of D25; or
  a heavy chain comprising the CDR1, CDR2, and CDR3 sequences of AM14 and a light chain comprising the CDR1, CDR2, and CDR3 sequences of AM14; or
  a heavy chain comprising the CDR1, CDR2, and CDR3 sequences of AM16 and a light chain comprising the CDR1, CDR2, and CDR3 sequences of AM16; or
  a heavy chain comprising the CDR1, CDR2, and CDR3 sequences of AM23 and a light chain comprising the CDR1, CDR2, and CDR3 sequences of AM23.

13. A method for treating and/or preventing a RSV-related disorder, the method comprising administering to an individual in need thereof a therapeutically effective amount of the antibody or functional part thereof of claim 2.

14. A method for treating and/or preventing a RSV-related disorder, the method comprising administering to an individual in need thereof a therapeutically effective amount of the antibody or functional part thereof of claim 4.

15. A method for treating and/or preventing a RSV-related disorder, the method comprising administering to an individual in need thereof a therapeutically effective amount of the pharmaceutical composition of claim 6.

16. A method for treating and/or preventing a RSV-related disorder, the method comprising administering to an individual in need thereof a therapeutically effective amount of the pharmaceutical composition of claim 7.

17. A method for treating and/or preventing a RSV-related disorder, the method comprising administering to an individual in need thereof a therapeutically effective amount of the pharmaceutical composition of claim 8.

18. A method for treating and/or preventing a RSV-related disorder, the method comprising administering to an individual in need thereof a therapeutically effective amount of the pharmaceutical composition of claim 11.

19. A method for treating and/or preventing a RSV-related disorder, the method comprising administering to an individual in need thereof a therapeutically effective amount of the pharmaceutical composition of claim 12.

* * * * *

SEQUENCE LISTING

<160> NUMBER OF SEQ ID NOS: 32

<210> SEQ ID NO 1
<211> LENGTH: 90
<212> TYPE: DNA
<213> ORGANISM: Artificial
<220> FEATURE:
<223> OTHER INFORMATION: anti-RSV antibody heavy chain Fw1
<220> FEATURE:
<221> NAME/KEY: CDS
<222> LOCATION: (1)..(90)

<400> SEQUENCE: 1

```
cag gtc cag ctg gta cag tct ggg gct gag gtg aag aag ccc ggg gcc    48
Gln Val Gln Leu Val Gln Ser Gly Ala Glu Val Lys Lys Pro Gly Ala
1               5                   10                  15 aca gtg aaa gtc tcc tgc aag att tcc gga cac acc ctc att            90
Thr Val Lys Val Ser Cys Lys Ile Ser Gly His Thr Leu Ile
            20                  25                  30
```

<210> SEQ ID NO 2
<211> LENGTH: 30
<212> TYPE: PRT
<213> ORGANISM: Artificial
<220> FEATURE:
<223> OTHER INFORMATION: Synthetic Construct

<400> SEQUENCE: 2

```
Gln Val Gln Leu Val Gln Ser Gly Ala Glu Val Lys Lys Pro Gly Ala
1               5                   10                  15

Thr Val Lys Val Ser Cys Lys Ile Ser Gly His Thr Leu Ile
            20                  25                  30
```

<210> SEQ ID NO 3
<211> LENGTH: 15
<212> TYPE: DNA
<213> ORGANISM: Artificial
<220> FEATURE:
<223> OTHER INFORMATION: anti-RSC antibody heavy chain CDR1
<220> FEATURE:
<221> NAME/KEY: CDS
<222> LOCATION: (1)..(15)

<400> SEQUENCE: 3

```
aaa tta tcc att cac                                                15
Lys Leu Ser Ile His
1               5
```

<210> SEQ ID NO 4
<211> LENGTH: 5
<212> TYPE: PRT
<213> ORGANISM: Artificial
<220> FEATURE:
<223> OTHER INFORMATION: Synthetic Construct

<400> SEQUENCE: 4

```
Lys Leu Ser Ile His
1               5
```

<210> SEQ ID NO 5
<211> LENGTH: 42
<212> TYPE: DNA
<213> ORGANISM: Artificial
<220> FEATURE:
<223> OTHER INFORMATION: anti-RSV antibody heavy chain Fw2
<220> FEATURE:
<221> NAME/KEY: CDS
<222> LOCATION: (1)..(42)

-continued

<400> SEQUENCE: 5

```
tgg gtg cga cag gct cct gga aag ggg ctt gag tgg atg gga        42
Trp Val Arg Gln Ala Pro Gly Lys Gly Leu Glu Trp Met Gly
1               5                   10
```

<210> SEQ ID NO 6
<211> LENGTH: 14
<212> TYPE: PRT
<213> ORGANISM: Artificial
<220> FEATURE:
<223> OTHER INFORMATION: Synthetic Construct

<400> SEQUENCE: 6

```
Trp Val Arg Gln Ala Pro Gly Lys Gly Leu Glu Trp Met Gly
1               5                   10
```

<210> SEQ ID NO 7
<211> LENGTH: 51
<212> TYPE: DNA
<213> ORGANISM: Artificial
<220> FEATURE:
<223> OTHER INFORMATION: anti-RSV antibody heavy chain CDR2
<220> FEATURE:
<221> NAME/KEY: CDS
<222> LOCATION: (1)..(51)

<400> SEQUENCE: 7

```
ggt tat gag ggt gag gtc gat gag att ttc tac gca cag aag ttc cag    48
Gly Tyr Glu Gly Glu Val Asp Glu Ile Phe Tyr Ala Gln Lys Phe Gln
1               5                   10                  15 cac                                                                51
His
```

<210> SEQ ID NO 8
<211> LENGTH: 17
<212> TYPE: PRT
<213> ORGANISM: Artificial
<220> FEATURE:
<223> OTHER INFORMATION: Synthetic Construct

<400> SEQUENCE: 8

```
Gly Tyr Glu Gly Glu Val Asp Glu Ile Phe Tyr Ala Gln Lys Phe Gln
1               5                   10                  15

His
```

<210> SEQ ID NO 9
<211> LENGTH: 96
<212> TYPE: DNA
<213> ORGANISM: Artificial
<220> FEATURE:
<223> OTHER INFORMATION: anti-RSV antibody heavy chain Fw3
<220> FEATURE:
<221> NAME/KEY: CDS
<222> LOCATION: (1)..(96)

<400> SEQUENCE: 9

```
aga ctc acc gtg atc gcc gac aca gcg aca gac aca gtc tac atg gaa    48
Arg Leu Thr Val Ile Ala Asp Thr Ala Thr Asp Thr Val Tyr Met Glu
1               5                   10                  15 ctg ggc agg ctc acc tct gac gac acg gcc gtc tat ttc tgt gga aca    96
Leu Gly Arg Leu Thr Ser Asp Asp Thr Ala Val Tyr Phe Cys Gly Thr
                20                  25                  30
```

<210> SEQ ID NO 10
<211> LENGTH: 32

```
<212> TYPE: PRT
<213> ORGANISM: Artificial
<220> FEATURE:
<223> OTHER INFORMATION: Synthetic Construct

<400> SEQUENCE: 10

Arg Leu Thr Val Ile Ala Asp Thr Ala Thr Asp Thr Val Tyr Met Glu
1               5                   10                  15

Leu Gly Arg Leu Thr Ser Asp Asp Thr Ala Val Tyr Phe Cys Gly Thr
            20                  25                  30

<210> SEQ ID NO 11
<211> LENGTH: 45
<212> TYPE: DNA
<213> ORGANISM: Artificial
<220> FEATURE:
<223> OTHER INFORMATION: anti-RSV antibody heavy chain CDR3
<220> FEATURE:
<221> NAME/KEY: CDS
<222> LOCATION: (1)..(45)

<400> SEQUENCE: 11 cta ggt gtg aca gtg act gag gct gga ctg ggg atc gat gac tac          45
Leu Gly Val Thr Val Thr Glu Ala Gly Leu Gly Ile Asp Asp Tyr
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic Construct

<400> SEQUENCE: 12

Leu Gly Val Thr Val Thr Glu Ala Gly Leu Gly Ile Asp Asp Tyr
1               5                   10                  15

<210> SEQ ID NO 13
<211> LENGTH: 33
<212> TYPE: DNA
<213> ORGANISM: Artificial
<220> FEATURE:
<223> OTHER INFORMATION: anti-RSV antibody heavy chain Fw4
<220> FEATURE:
<221> NAME/KEY: CDS
<222> LOCATION: (1)..(33)

<400> SEQUENCE: 13 tgg ggc cag gga acc ctg gtc acc gtc tcc tca                          33
Trp Gly Gln Gly Thr Leu Val Thr Val Ser Ser
1               5                   10

<210> SEQ ID NO 14
<211> LENGTH: 11
<212> TYPE: PRT
<213> ORGANISM: Artificial
<220> FEATURE:
<223> OTHER INFORMATION: Synthetic Construct

<400> SEQUENCE: 14

Trp Gly Gln Gly Thr Leu Val Thr Val Ser Ser
1               5                   10

<210> SEQ ID NO 15
<211> LENGTH: 372
<212> TYPE: DNA
<213> ORGANISM: Artificial
<220> FEATURE:
```

<223> OTHER INFORMATION: Anti-RSV antibody heavy chain
<220> FEATURE:
<221> NAME/KEY: CDS
<222> LOCATION: (1)..(372)

<400> SEQUENCE: 15

```
cag gtc cag ctg gta cag tct ggg gct gag gtg aag aag ccc ggg gcc        48
Gln Val Gln Leu Val Gln Ser Gly Ala Glu Val Lys Lys Pro Gly Ala
1               5                   10                  15 aca gtg aaa gtc tcc tgc aag att tcc gga cac acc ctc att aaa tta        96
Thr Val Lys Val Ser Cys Lys Ile Ser Gly His Thr Leu Ile Lys Leu
            20                  25                  30 tcc att cac tgg gtg cga cag gct cct gga aag ggg ctt gag tgg atg       144
Ser Ile His Trp Val Arg Gln Ala Pro Gly Lys Gly Leu Glu Trp Met
        35                  40                  45 gga ggt tat gag ggt gag gtc gat gag att ttc tac gca cag aag ttc       192
Gly Gly Tyr Glu Gly Glu Val Asp Glu Ile Phe Tyr Ala Gln Lys Phe
    50                  55                  60 cag cac aga ctc acc gtg atc gcc gac aca gcg aca gac aca gtc tac       240
Gln His Arg Leu Thr Val Ile Ala Asp Thr Ala Thr Asp Thr Val Tyr
65                  70                  75                  80 atg gaa ctg ggc agg ctc acc tct gac gac acg gcc gtc tat ttc tgt       288
Met Glu Leu Gly Arg Leu Thr Ser Asp Asp Thr Ala Val Tyr Phe Cys
                85                  90                  95 gga aca cta ggt gtg aca gtg act gag gct gga ctg ggg atc gat gac       336
Gly Thr Leu Gly Val Thr Val Thr Glu Ala Gly Leu Gly Ile Asp Asp
            100                 105                 110 tac tgg ggc cag gga acc ctg gtc acc gtc tcc tca                       372
Tyr Trp Gly Gln Gly Thr Leu Val Thr Val Ser Ser
        115                 120
```

<210> SEQ ID NO 16
<211> LENGTH: 124
<212> TYPE: PRT
<213> ORGANISM: Artificial
<220> FEATURE:
<223> OTHER INFORMATION: Synthetic Construct

<400> SEQUENCE: 16

```
Gln Val Gln Leu Val Gln Ser Gly Ala Glu Val Lys Lys Pro Gly Ala
1               5                   10                  15

Thr Val Lys Val Ser Cys Lys Ile Ser Gly His Thr Leu Ile Lys Leu
            20                  25                  30

Ser Ile His Trp Val Arg Gln Ala Pro Gly Lys Gly Leu Glu Trp Met
        35                  40                  45

Gly Gly Tyr Glu Gly Glu Val Asp Glu Ile Phe Tyr Ala Gln Lys Phe
    50                  55                  60

Gln His Arg Leu Thr Val Ile Ala Asp Thr Ala Thr Asp Thr Val Tyr
65                  70                  75                  80

Met Glu Leu Gly Arg Leu Thr Ser Asp Asp Thr Ala Val Tyr Phe Cys
                85                  90                  95

Gly Thr Leu Gly Val Thr Val Thr Glu Ala Gly Leu Gly Ile Asp Asp
            100                 105                 110

Tyr Trp Gly Gln Gly Thr Leu Val Thr Val Ser Ser
        115                 120
```

<210> SEQ ID NO 17
<211> LENGTH: 69
<212> TYPE: DNA
<213> ORGANISM: Artificial
<220> FEATURE:

<223> OTHER INFORMATION: anti-RSV antibody light chain Fw1
<220> FEATURE:
<221> NAME/KEY: CDS
<222> LOCATION: (1)..(69)

<400> SEQUENCE: 17

```
gaa att gtg ttg aca cag tct cca ggc acc ctg tct ttg tct cca gga    48
Glu Ile Val Leu Thr Gln Ser Pro Gly Thr Leu Ser Leu Ser Pro Gly
1               5                   10                  15 gaa aga gcc acc ctc tcc tgc                                        69
Glu Arg Ala Thr Leu Ser Cys
            20
```

<210> SEQ ID NO 18
<211> LENGTH: 23
<212> TYPE: PRT
<213> ORGANISM: Artificial
<220> FEATURE:
<223> OTHER INFORMATION: Synthetic Construct

<400> SEQUENCE: 18

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 19
<211> LENGTH: 36
<212> TYPE: DNA
<213> ORGANISM: Artificial
<220> FEATURE:
<223> OTHER INFORMATION: Anti-RSV antibody light chain CDR1
<220> FEATURE:
<221> NAME/KEY: CDS
<222> LOCATION: (1)..(36)

<400> SEQUENCE: 19

```
agg gcc agt cag att gtt agc agg aac cac tta gcc                    36
Arg Ala Ser Gln Ile Val Ser Arg Asn His Leu Ala
1               5                   10
```

<210> SEQ ID NO 20
<211> LENGTH: 12
<212> TYPE: PRT
<213> ORGANISM: Artificial
<220> FEATURE:
<223> OTHER INFORMATION: Synthetic Construct

<400> SEQUENCE: 20

```
Arg Ala Ser Gln Ile Val Ser Arg Asn His Leu Ala
1               5                   10
```

<210> SEQ ID NO 21
<211> LENGTH: 45
<212> TYPE: DNA
<213> ORGANISM: Artificial
<220> FEATURE:
<223> OTHER INFORMATION: anti-RSV antibody light chain Fw2
<220> FEATURE:
<221> NAME/KEY: CDS
<222> LOCATION: (1)..(45)

<400> SEQUENCE: 21

```
tgg tac cag caa aaa cct ggc cag gct ccc agg ctc ctc atc ttt        45
Trp Tyr Gln Gln Lys Pro Gly Gln Ala Pro Arg Leu Leu Ile Phe
1               5                   10                  15
```

```
<210> SEQ ID NO 22
<211> LENGTH: 15
<212> TYPE: PRT
<213> ORGANISM: Artificial
<220> FEATURE:
<223> OTHER INFORMATION: Synthetic Construct

<400> SEQUENCE: 22

Trp Tyr Gln Gln Lys Pro Gly Gln Ala Pro Arg Leu Leu Ile Phe
1               5                   10                  15

<210> SEQ ID NO 23
<211> LENGTH: 21
<212> TYPE: DNA
<213> ORGANISM: Artificial
<220> FEATURE:
<223> OTHER INFORMATION: anti-RSV antibody light chain CDR2
<220> FEATURE:
<221> NAME/KEY: CDS
<222> LOCATION: (1)..(21)

<400> SEQUENCE: 23 ggt gcg tcc agt cgg gcc act                                          21
Gly Ala Ser Ser Arg Ala Thr
1               5

<210> SEQ ID NO 24
<211> LENGTH: 7
<212> TYPE: PRT
<213> ORGANISM: Artificial
<220> FEATURE:
<223> OTHER INFORMATION: Synthetic Construct

<400> SEQUENCE: 24

Gly Ala Ser Ser Arg Ala Thr
1               5

<210> SEQ ID NO 25
<211> LENGTH: 96
<212> TYPE: DNA
<213> ORGANISM: Artificial
<220> FEATURE:
<223> OTHER INFORMATION: Anti-RSV antibody light chain Fw3
<220> FEATURE:
<221> NAME/KEY: CDS
<222> LOCATION: (1)..(96)

<400> SEQUENCE: 25 ggc atc cca gtc cgg ttc agt ggc agt ggg tct ggg aca gac ttc act      48
Gly Ile Pro Val Arg Phe Ser Gly Ser Gly Ser Gly Thr Asp Phe Thr
1               5                   10                  15 ctc acc atc aac gga ctg gcg cct gaa gat ttt gca gtt tac tac tgt      96
Leu Thr Ile Asn Gly Leu Ala Pro Glu Asp Phe Ala Val Tyr Tyr Cys
            20                  25                  30

<210> SEQ ID NO 26
<211> LENGTH: 32
<212> TYPE: PRT
<213> ORGANISM: Artificial
<220> FEATURE:
<223> OTHER INFORMATION: Synthetic Construct

<400> SEQUENCE: 26

Gly Ile Pro Val Arg Phe Ser Gly Ser Gly Ser Gly Thr Asp Phe Thr
1               5                   10                  15

Leu Thr Ile Asn Gly Leu Ala Pro Glu Asp Phe Ala Val Tyr Tyr Cys
            20                  25                  30
```

<210> SEQ ID NO 27
<211> LENGTH: 21
<212> TYPE: DNA
<213> ORGANISM: Artificial
<220> FEATURE:
<223> OTHER INFORMATION: Anti-RSV antibody light chain CDR3
<220> FEATURE:
<221> NAME/KEY: CDS
<222> LOCATION: (1)..(21)

<400> SEQUENCE: 27

```
ctg tcc tct gat tcc tcc ata                                    21
Leu Ser Ser Asp Ser Ser Ile
1               5
```

<210> SEQ ID NO 28
<211> LENGTH: 7
<212> TYPE: PRT
<213> ORGANISM: Artificial
<220> FEATURE:
<223> OTHER INFORMATION: Synthetic Construct

<400> SEQUENCE: 28

```
Leu Ser Ser Asp Ser Ser Ile
1               5
```

<210> SEQ ID NO 29
<211> LENGTH: 36
<212> TYPE: DNA
<213> ORGANISM: Artificial
<220> FEATURE:
<223> OTHER INFORMATION: Anti-RSV antibody light chain Fw4
<220> FEATURE:
<221> NAME/KEY: CDS
<222> LOCATION: (1)..(36)

<400> SEQUENCE: 29

```
ttc aca ttc ggc cct ggg acc aag gtg gat ttc aaa                36
Phe Thr Phe Gly Pro Gly Thr Lys Val Asp Phe Lys
1               5                   10
```

<210> SEQ ID NO 30
<211> LENGTH: 12
<212> TYPE: PRT
<213> ORGANISM: Artificial
<220> FEATURE:
<223> OTHER INFORMATION: Synthetic Construct

<400> SEQUENCE: 30

```
Phe Thr Phe Gly Pro Gly Thr Lys Val Asp Phe Lys
1               5                   10
```

<210> SEQ ID NO 31
<211> LENGTH: 324
<212> TYPE: DNA
<213> ORGANISM: Artificial
<220> FEATURE:
<223> OTHER INFORMATION: Anti-RSV antibody light chain
<220> FEATURE:
<221> NAME/KEY: CDS
<222> LOCATION: (1)..(324)

<400> SEQUENCE: 31

```
gaa att gtg ttg aca cag tct cca ggc acc ctg tct ttg tct cca gga    48
Glu Ile Val Leu Thr Gln Ser Pro Gly Thr Leu Ser Leu Ser Pro Gly
1               5                   10                  15 gaa aga gcc acc ctc tcc tgc agg gcc agt cag att gtt agc agg aac    96
Glu Arg Ala Thr Leu Ser Cys Arg Ala Ser Gln Ile Val Ser Arg Asn
```

-continued

```
                  20                  25                  30
cac tta gcc tgg tac cag caa aaa cct ggc cag gct ccc agg ctc ctc      144
His Leu Ala Trp Tyr Gln Gln Lys Pro Gly Gln Ala Pro Arg Leu Leu
            35                  40                  45 atc ttt ggt gcg tcc agt cgg gcc act ggc atc cca gtc cgg ttc agt      192
Ile Phe Gly Ala Ser Ser Arg Ala Thr Gly Ile Pro Val Arg Phe Ser
 50                  55                  60 ggc agt ggg tct ggg aca gac ttc act ctc acc atc aac gga ctg gcg      240
Gly Ser Gly Ser Gly Thr Asp Phe Thr Leu Thr Ile Asn Gly Leu Ala
 65                  70                  75                  80 cct gaa gat ttt gca gtt tac tac tgt ctg tcc tct gat tcc tcc ata      288
Pro Glu Asp Phe Ala Val Tyr Tyr Cys Leu Ser Ser Asp Ser Ser Ile
                85                  90                  95 ttc aca ttc ggc cct ggg acc aag gtg gat ttc aaa                      324
Phe Thr Phe Gly Pro Gly Thr Lys Val Asp Phe Lys
            100                 105
```

<210> SEQ ID NO 32
<211> LENGTH: 108
<212> TYPE: PRT
<213> ORGANISM: Artificial
<220> FEATURE:
<223> OTHER INFORMATION: Synthetic Construct

<400> SEQUENCE: 32

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ile Val Ser Arg Asn
                20                  25                  30

His Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Val Arg Phe Ser
 50                  55                  60

Gly Ser Gly Ser Gly Thr Asp Phe Thr Leu Thr Ile Asn Gly Leu Ala
 65                  70                  75                  80

Pro Glu Asp Phe Ala Val Tyr Tyr Cys Leu Ser Ser Asp Ser Ser Ile
                85                  90                  95

Phe Thr Phe Gly Pro Gly Thr Lys Val Asp Phe Lys
            100                 105
```